United States Patent [19]

Pestka et al.

[11] Patent Number: 5,843,697

[45] Date of Patent: Dec. 1, 1998

[54] CELLS EXPRESSING IL-10 RECEPTOR AND THE CRFB4 GENE PRODUCT, AN IL-10 RECEPTOR ACCESSORY PROTEIN

[75] Inventors: Sidney Pestka, North Caldwell; Serguei V. Kotenko, Highland Park, both of N.J.

[73] Assignee: University of Medicine and Dentistry of New Jersey, Piscataway, N.J.

[21] Appl. No.: 683,743

[22] Filed: Jul. 17, 1996

[51] Int. Cl.[6] .......... C12N 15/12; C07K 14/715; G01N 33/53

[52] U.S. Cl. .......... 435/29; 435/325; 435/320.1; 435/7.21; 536/23.5

[58] Field of Search .................. 435/320.1, 325, 435/29, 7.21; 536/23.5

[56] References Cited

PUBLICATIONS

Soh, J., et al. (1994) *J. Biol. Chem.* 269: 18102–10.
Cook, J. R., et al. (1996) *J. Biol. Chem.* 271: 13448–53.
Lutfalla, G., et al. (1993) *Genomics* 16: 366–73.
Ho, A. S.–Y., et al. (1994) *Ther. Immunol.* 1: 173–85.
Liu, Y., et al. (1997) *J. Immunol.* 158: 604–13.
Pestka, S. (1997) *Semin. Oncol.* 24 (Suppl. 9): S9–18–20.

*Primary Examiner*—David L. Fitzgerald
*Attorney, Agent, or Firm*—Klauber & Jackson

[57] ABSTRACT

The present invention relates to the identification of intracellular signal transduction function for a putative cytokine receptor subunit. In particular, the invention relates to the identification of the signal transduction protein for the interleukin (IL)-10 receptor. Accordingly, the present invention relates to preparing recombinant cells that express the IL-10 receptor and the newly identified IL-10 signal transduction protein, e.g., for use in screening libraries of compounds for IL-10 agonists and antagonists; to restoring IL-10 function to cells in vivo, e.g., via gene therapy; and in addition to chimeric proteins comprising this signal transduction protein to agonize IL-10 activity. In specific examples, cells transfected with both the first chain of the IL-10R and the presently identified second chain, termed herein CRFB4, were able to transduce a signal in response to contact with IL-10.

16 Claims, 11 Drawing Sheets

FIG.5A

| | γR2 | | γR2/γR1 | | γR2/αR2 | | γR2/αR1 | | γR2/CRF | |
|---|---|---|---|---|---|---|---|---|---|---|
| IFN-γ | − | + | − | + | − | + | − | + | − | + |

I.P.: anti-Jak2

Jak2-P →

Blot: anti-P-Tyr

Jak2 →

Blot: anti-Jak2

FIG.5B

I.P.: anti-Tyk2

Tyk2-P →

Blot: anti-P-Tyr

Tyk2 →

Blot: anti-Tyk2

FIG.5C

| | γR2/αR1 | | γR2/CRF | | COS-1/Tyk2 |
|---|---|---|---|---|---|
| IFN-γ | − | + | − | + | |

I.P.: anti-P-Tyr

Tyk2-P →

FIG.5D

| γR2/αR1 | γR2/αR1+Tyk2 |
|---|---|

I.P.: anti-Tyk2

← Tyk2

Blot: anti-Tyk2 pEF2-IL-10R/γR1 pEF2-IL-10R/γR1-CRF

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 3632 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:1:

```
AAAGAGCTGG  AGGCGCGCAG  GCCGGCTCCG  CTCCGGCCCC  GGACGATGCG  GCGCGCCCAG    60
GATGCTGCCG  TGCCTCGTAG  TGCTGCTGGC  GGCGCTCCTC  AGCCTCCGTC  TTGGCTCAGA   120
CGCTCATGGG  ACAGAGCTGC  CCAGCCCTCC  GTCTGTGTGG  TTTGAAGCAG  AATTTTTCCA   180
CCACATCCTC  CACTGGACAC  CCATCCCAAA  TCAGTCTGAA  AGTACCTGCT  ATGAAGTGGC   240
GCTCCTGAGG  TATGGAATAG  AGTCCTGGAA  CTCCATCTCC  AACTGTAGCC  AGACCCTGTC   300
CTATGACCTT  ACCGCAGTGA  CCTTGGACCT  GTACCACAGC  AATGGCTACC  GGGCCAGAGT   360
GCGGGCTGTG  GACGGCAGCC  GGCACTCCAA  CTGGACCGTC  ACCAACACCC  GCTTCTCTGT   420
GGATGAAGTG  ACTCTGACAG  TTGGCAGTGT  GAACCTAGAG  ATCCACAATG  GCTTCATCCT   480
CGGGAAGATT  CAGCTACCCA  GGCCCAAGAT  GGCCCCGCG   AATGACACAT  ATGAAAGCAT   540
CTTCAGTCAC  TTCCGAGAGT  ATGAGATTGC  CATTCGCAAG  GTGCCGGGAA  ACTTCACGTT   600
CACACACAAG  AAAGTAAAAC  ATGAAAACTT  CAGCCTCCTA  ACCTCTGGAG  AAGTGGGAGA   660
GTTCTGTGTC  CAGGTGAAAC  CATCTGTCGC  TTCCCGAAGT  AACAAGGGGA  TGTGGTCTAA   720
AGAGGAGTGC  ATCTCCCTCA  CCAGGCAGTA  TTTCACCGTG  ACCAACGTCA  TCATCTTCTT   780
TGCCTTTGTC  CTGCTGCTCT  CCGGAGCCCT  CGCCTACTGC  CTGGCCCTCC  AGCTGTATGT   840
GCGGCGCCGA  AAGAAGCTAC  CCAGTGTCCT  GCTCTTCAAG  AAGCCCAGCC  CCTTCATCTT   900
CATCAGCCAG  CGTCCCTCCC  CAGAGACCCA  AGACACCATC  CACCCGCTTG  ATGAGGAGGC   960
CTTTTTGAAG  GTGTCCCCAG  AGCTGAAGAA  CTTGGACCTG  CACGGCAGCA  CAGACAGTGG  1020
CTTTGGCAGC  ACCAAGCCAT  CCCTGCAGAC  TGAAGAGCCC  CAGTTCCTCC  TCCCTGACCC  1080
TCACCCCCAG  GCTGACAGAA  CGCTGGGAAA  CGGGGAGCCC  CCTGTGCTGG  GGACAGCTG   1140
CAGTAGTGGC  AGCAGCAATA  GCACAGACAG  CGGGATCTGC  CTGCAGGAGC  CCAGCCTGAG  1200
CCCCAGCACA  GGGCCCACCT  GGGAGCAACA  GGTGGGGAGC  AACAGCAGGG  GCCAGGATGA  1260
CAGTGGCATT  GACTTAGTTC  AAAACTCTGA  GGGCCGGGCT  GGGGACACAC  AGGGTGGCTC  1320
GGCCTTGGGC  CACCACAGTC  CCCCGGAGCC  TGAGGTGCCT  GGGGAAGAAG  ACCCAGCTGC  1380
TGTGGCATTC  CAGGGTTACC  TGAGGCAGAC  CAGATGTGCT  GAAGAGAAGG  CAACCAAGAC  1440
AGGCTGCCTG  GAGGAAGAAT  CGCCCTTGAC  AGATGGCCTT  GGCCCCAAAT  TCGGGAGATG  1500
CCTGGTTGAT  GAGGCAGGCT  TGCATCCACC  AGCCCTGGCC  AAGGGCTATT  TGAAACAGGA  1560
TCCTCTAGAA  ATGACTCTGG  CTTCCTCAGG  GGCCCCAACG  GGACAGTGGA  ACCAGCCCAC  1620
TGAGGAATGG  TCACTCCTGG  CCTTGAGCAG  CTGCAGTGAC  CTGGAATAT   CTGACTGGAG  1680
CTTTGCCCAT  GACCTTGCCC  CTCTAGGCTG  TGTGGCAGCC  CCAGGTGGTC  TCCTGGGCAG  1740
```

-continued

| | | | | | | |
|---|---|---|---|---|---|---|
| CTTTAACTCA | GACCTGGTCA | CCCTGCCCCT | CATCTCTAGC | CTGCAGTCAA | GTGAGTGACT | 1800 |
| CGGGCTGAGA | GGCTGCTTTT | GATTTTAGCC | ATGCCTGCTC | CTCTGCCTGG | ACCAGGAGGA | 1860 |
| GGGCCCTGGG | GCAGAAGTTA | GGCACGAGGC | AGTCTGGGCA | CTTTTCTGCA | AGTCCACTGG | 1920 |
| GGCTGGCCCA | GCCAGGCTGC | AGGGCTGGTC | AGGGTGTCTG | GGGCAGGAGG | AGGCCAACTC | 1980 |
| ACTGAACTAG | TGCAGGGTAT | GTGGGTGGCA | CTGACCTGTT | CTGTTGACTG | GGGCCCTGCA | 2040 |
| GACTCTGGCA | GAGCTGAGAA | GGGCAGGGAC | CTTCTCCCTC | CTAGGAACTC | TTTCCTGTAT | 2100 |
| CATAAAGGAT | TATTTGCTCA | GGGGAACCAT | GGGGCTTTCT | GGAGTTGTGG | TGAGGCCACC | 2160 |
| AGGCTGAAGT | CAGCTCAGAC | CCAGACCTCC | CTGCTTAGGC | CACTCGAGCA | TCAGAGCTTC | 2220 |
| CAGCAGGAGG | AAGGGCTGTA | GGAATGGAAG | CTTCAGGGCC | TTGCTGCTGG | GGTCATTTTT | 2280 |
| AGGGGAAAAA | GGAGGATATG | ATGGTCACAT | GGGGAACCTC | CCCTCATCGG | GCCTCTGGGG | 2340 |
| CAGGAAGCTT | GTCACTGGAA | GATCTTAAGG | TATATATTTT | CTGGACACTC | AAACACATCA | 2400 |
| TAATGGATTC | ACTGAGGGGA | GACAAAGGGA | GCCGAGACCC | TGGATGGGGC | TTCCAGCTCA | 2460 |
| GAACCCATCC | CTCTGGTGGG | TACCTCTGGC | ACCCATCTGC | AAATATCTCC | CTCTCTCCAA | 2520 |
| CAAATGGAGT | AGCATCCCCC | TGGGGCACTT | GCTGAGGCCA | AGCCACTCAC | ATCCTCACTT | 2580 |
| TGCTGCCCCA | CCATCTTGCT | GACAACTTCC | AGAGAAGCCA | TGGTTTTTG | TATTGGTCAT | 2640 |
| AACTCAGCCC | TTTGGGCGGC | CTCTGGGCTT | GGGCACCAGC | TCATGCCAGC | CCCAGAGGGT | 2700 |
| CAGGGTTGGA | GGCCTGTGCT | TGTGTTTGCT | GCTAATGTCC | AGCTACAGAC | CCAGAGGATA | 2760 |
| AGCCACTGGG | CACTGGGCTG | GGGTCCCTGC | CTTGTTGGTG | TTCAGCTGTG | TGATTTTGGA | 2820 |
| CTAGCCACTT | GTCAGAGGGC | CTCAATCTCC | CATCTGTGAA | ATAAGGACTC | CACCTTTAGG | 2880 |
| GGACCCTCCA | TGTTTGCTGG | GTATTAGCCA | AGCTGGTCCT | GGGAGAATGC | AGATACTGTC | 2940 |
| CGTGGACTAC | CAAGCTGGCT | TGTTTCTTAT | GCCAGAGGCT | AACAGATCCA | ATGGGAGTCC | 3000 |
| ATGGTGTCAT | GCCAAGACAG | TATCAGACAC | AGCCCCAGAA | GGGGGCATTA | TGGGCCCTGC | 3060 |
| CTCCCCATAG | GCCATTTGGA | CTCTGCCTTC | AAACAAAGGC | AGTTCAGTCC | ACAGGCATGG | 3120 |
| AAGCTGTGAG | GGGACAGGCC | TGTGCGTGCC | ATCCAGAGTC | ATCTCAGCCC | TGCCTTTCTC | 3180 |
| TGGAGCATTC | TGAAAACAGA | TATTCTGGCC | CAGGGAATCC | AGCCATGACC | CCCACCCCTC | 3240 |
| TGCCAAAGTA | CTCTTAGGTG | CCAGTCTGGT | AACTGAACTC | CCTCTGGAGG | CAGGCTTGAG | 3300 |
| GGAGGATTCC | TCAGGGTTCC | CTTGAAAGCT | TTATTTATTT | ATTTGTTCA | TTTATTTATT | 3360 |
| GGAGAGGCAG | CATTGCACAG | TGAAAGAATT | CTGGATATCT | CAGGAGCCCC | GAAATTCTAG | 3420 |
| CTCTGACTTT | GCTGTTTCCA | GTGGTATGAC | CTTGGAGAAG | TCACTTATCC | TCTTGGAGCC | 3480 |
| TCAGTTTCCT | CATCTGCAGA | ATAATGACTG | ACTTGTCTAA | TTCATAGGGA | TGTGAGGTTC | 3540 |
| TGCTGAGGAA | ATGGGTATGA | ATGTGCCTTG | AACACAAAGC | TCTGTCAATA | AGTGATACAT | 3600 |
| GTTTTTTATT | CCAATAAATT | GTCAAGACCA | CA | | | 3632 |

( 2 ) INFORMATION FOR SEQ ID NO:2:

( i ) SEQUENCE CHARACTERISTICS:
        ( A ) LENGTH: 578 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v ) FRAGMENT TYPE:

( x i ) SEQUENCE DESCRIPTION: SEQ ID NO:2:

```
Met  Leu  Pro  Cys  Leu  Val  Val  Leu  Leu  Ala  Ala  Leu  Leu  Ser  Leu  Arg
 1              5                   10                        15

Leu  Gly  Ser  Asp  Ala  His  Gly  Thr  Glu  Leu  Pro  Ser  Pro  Pro  Ser  Val
               20                   25                   30

Trp  Phe  Glu  Ala  Glu  Phe  Phe  His  Ile  Leu  His  Trp  Thr  Pro  Ile
          35                        40                   45

Pro  Asn  Gln  Ser  Glu  Ser  Thr  Cys  Tyr  Glu  Val  Ala  Leu  Leu  Arg  Tyr
     50                   55                        60

Gly  Ile  Glu  Ser  Trp  Asn  Ser  Ile  Ser  Asn  Cys  Ser  Gln  Thr  Leu  Ser
 65                 70                        75                             80

Tyr  Asp  Leu  Thr  Ala  Val  Thr  Leu  Asp  Leu  Tyr  His  Ser  Asn  Gly  Tyr
               85                   90                        95

Arg  Ala  Arg  Val  Arg  Ala  Val  Asp  Gly  Ser  Arg  His  Ser  Asn  Trp  Thr
               100                  105                       110

Val  Thr  Asn  Thr  Arg  Phe  Ser  Val  Asp  Glu  Val  Thr  Leu  Thr  Val  Gly
               115                 120                       125

Ser  Val  Asn  Leu  Glu  Ile  His  Asn  Gly  Phe  Ile  Leu  Gly  Lys  Ile  Gln
     130                       135                       140

Leu  Pro  Arg  Pro  Lys  Met  Ala  Pro  Ala  Asn  Asp  Thr  Tyr  Glu  Ser  Ile
145                      150                      155                       160

Phe  Ser  His  Phe  Arg  Glu  Tyr  Glu  Ile  Ala  Ile  Arg  Lys  Val  Pro  Gly
               165                       170                       175

Asn  Phe  Thr  Phe  Thr  His  Lys  Lys  Val  Lys  His  Glu  Asn  Phe  Ser  Leu
               180                       185                       190

Leu  Thr  Ser  Gly  Glu  Val  Gly  Glu  Phe  Cys  Val  Gln  Val  Lys  Pro  Ser
          195                       200                       205

Val  Ala  Ser  Arg  Ser  Asn  Lys  Gly  Met  Trp  Ser  Lys  Glu  Glu  Cys  Ile
     210                       215                       220

Ser  Leu  Thr  Arg  Gln  Tyr  Phe  Thr  Val  Thr  Asn  Val  Ile  Ile  Phe  Phe
225                            230                       235                  240

Ala  Phe  Val  Leu  Leu  Leu  Ser  Gly  Ala  Leu  Ala  Tyr  Cys  Leu  Ala  Leu
               245                       250                       255

Gln  Leu  Tyr  Val  Arg  Arg  Arg  Lys  Lys  Leu  Pro  Ser  Val  Leu  Leu  Phe
               260                       265                       270

Lys  Lys  Pro  Ser  Pro  Phe  Ile  Phe  Ile  Ser  Gln  Arg  Pro  Ser  Pro  Glu
               275                       280                       285

Thr  Gln  Asp  Thr  Ile  His  Pro  Leu  Asp  Glu  Glu  Ala  Phe  Leu  Lys  Val
     290                       295                       300

Ser  Pro  Glu  Leu  Lys  Asn  Leu  Asp  Leu  His  Gly  Ser  Thr  Asp  Ser  Gly
305                       310                       315                       320

Phe  Gly  Ser  Thr  Lys  Pro  Ser  Leu  Gln  Thr  Glu  Glu  Pro  Gln  Phe  Leu
               325                       330                       335

Leu  Pro  Asp  Pro  His  Pro  Gln  Ala  Asp  Arg  Thr  Leu  Gly  Asn  Gly  Glu
               340                       345                       350

Pro  Pro  Val  Leu  Gly  Asp  Ser  Cys  Ser  Ser  Gly  Ser  Ser  Asn  Ser  Thr
               355                       360                       365

Asp  Ser  Gly  Ile  Cys  Leu  Gln  Glu  Pro  Ser  Leu  Ser  Pro  Ser  Thr  Gly
     370                       375                       380

Pro  Thr  Trp  Glu  Gln  Gln  Val  Gly  Ser  Asn  Ser  Arg  Gly  Gln  Asp  Asp
385                       390                       395                       400

Ser  Gly  Ile  Asp  Leu  Val  Gln  Asn  Ser  Glu  Gly  Arg  Ala  Gly  Asp  Thr
               405                       410                       415

Gln  Gly  Gly  Ser  Ala  Leu  Gly  His  His  Ser  Pro  Pro  Glu  Pro  Glu  Val
```

| | | | | | 420 | | | | | 425 | | | | | 430 | |
|---|---|---|---|---|---|---|---|---|---|---|---|---|---|---|---|---|
| | Pro | Gly | Glu 435 | Glu | Asp | Pro | Ala | Ala 440 | Val | Ala | Phe | Gln | Gly 445 | Tyr | Leu | Arg |
| | Gln | Thr 450 | Arg | Cys | Ala | Glu | Glu 455 | Lys | Ala | Thr | Lys | Thr 460 | Gly | Cys | Leu | Glu |
| | Glu 465 | Glu | Ser | Pro | Leu | Thr 470 | Asp | Gly | Leu | Gly | Pro 475 | Lys | Phe | Gly | Arg | Cys 480 |
| | Leu | Val | Asp | Glu | Ala 485 | Gly | Leu | His | Pro | Pro 490 | Ala | Leu | Ala | Lys | Gly 495 | Tyr |
| | Leu | Lys | Gln | Asp 500 | Pro | Leu | Glu | Met | Thr 505 | Leu | Ala | Ser | Ser | Gly 510 | Ala | Pro |
| | Thr | Gly | Gln 515 | Trp | Asn | Gln | Pro | Thr 520 | Glu | Glu | Trp | Ser | Leu 525 | Leu | Ala | Leu |
| | Ser | Ser 530 | Cys | Ser | Asp | Leu | Gly 535 | Ile | Ser | Asp | Trp | Ser 540 | Phe | Ala | His | Asp |
| | Leu 545 | Ala | Pro | Leu | Gly | Cys 550 | Val | Ala | Ala | Pro | Gly 555 | Gly | Leu | Leu | Gly | Ser 560 |
| | Phe | Asn | Ser | Asp | Leu 565 | Val | Thr | Leu | Pro | Leu 570 | Ile | Ser | Ser | Leu | Gln 575 | Ser |
| | Ser | Glu | | | | | | | | | | | | | | |

( 2 ) INFORMATION FOR SEQ ID NO:3:

( i ) SEQUENCE CHARACTERISTICS:
        ( A ) LENGTH: 1875 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:3:

| | | | | | |
|---|---|---|---|---|---|
| GTCGTGTGCT | TGGAGGAAGC | CGCGGAACCC | CCAGCGTCCG | TCCATGGCGT | GGAGCCTTGG | 60 |
| GAGCTGGCTG | GGTGGCTGCC | TGCTGGTGTC | AGCATTGGGA | ATGGTACCAC | CTCCCGAAAA | 120 |
| TGTCAGAATG | AATTCTGTTA | ATTTCAAGAA | CATTCTACAG | TGGGAGTCAC | CTGCTTTTGC | 180 |
| CAAAGGGAAC | CTGACTTTCA | CAGCTCAGTA | CCTAAGTTAT | AGGATATTCC | AAGATAAATG | 240 |
| CATGAATACT | ACCTTGACGG | AATGTGATTT | CTCAAGTCTT | TCCAAGTATG | GTGACCACAC | 300 |
| CTTGAGAGTC | AGGGCTGAAT | TGCAGATGA | GCATTCAGAC | TGGGTAAACA | TCACCTTCTG | 360 |
| TCCTGTGGAT | GACACCATTA | TTGGACCCCC | TGGAATGCAA | GTAGAAGTAC | TTGCTGATTC | 420 |
| TTTACATATG | CGTTTCTTAG | CCCCTAAAAT | TGAGAATGAA | TACGAAACTT | GGACTATGAA | 480 |
| GAATGTGTAT | AACTCATGGA | CTTATAATGT | GCAATACTGG | AAAAACGGTA | CTGATGAAAA | 540 |
| GTTTCAAATT | ACTCCCCAGT | ATGACTTTGA | GGTCCTCAGA | AACCTGGAGC | CATGGACAAC | 600 |
| TTATTGTGTT | CAAGTTCGAG | GGTTTCTTCC | TGATCGGAAC | AAAGCTGGGG | AATGGAGTGA | 660 |
| GCCTGTCTGT | GAGCAAACAA | CCCATGACGA | AACGGTCCCC | TCCTGGATGG | TGGCCGTCAT | 720 |
| CCTCATGGCC | TCGGTCTTCA | TGGTCTGCCT | GGCACTCCTC | GGCTGCTTCT | CCTTGCTGTG | 780 |
| GTGCGTTTAC | AAGAAGACAA | AGTACGCCTT | CTCCCCTAGG | AATTCTCTTC | CACAGCACCT | 840 |
| GAAAGAGTTT | TTGGGCCATC | CTCATCATAA | CACACTTCTG | TTTTTCTCCT | TTCCATTGTC | 900 |
| GGATGAGAAT | GATGTTTTTG | ACAAGCTAAG | TGTCATTGCA | GAAGACTCTG | AGAGCGGCAA | 960 |
| GCAGAATCCT | GGTGACAGCT | GCAGCCTCGG | GACCCCGCCT | GGGCAGGGGC | CCAAAAGCTA | 1020 |

-continued

| | | | | | |
|---|---|---|---|---|---|
| GGCTCTGAGA | AGGAAACACA | CTCGGCTGGG | CACAGTGACG | TACTCCATCT | CACATCTGCC | 1080 |
| TCAGTGAGGG | ATCAGGGCAG | CAAACAAGGG | CCAAGACCAT | CTGAGCCAGC | CCCACATCTA | 1140 |
| GAACTCCAGA | CCTGGACTTA | GCCACCAGAG | AGCTACATTT | TAAAGGCTGT | CTTGGCAAAA | 1200 |
| ATACTCCATT | TGGGAACTCA | CTGCCTTATA | AAGGCTTTCA | TGATGTTTTC | AGAAGTTGGC | 1260 |
| CACTGAGAGT | GTAATTTTCA | GCCTTTTATA | TCACTAAAAT | AAGATCATGT | TTAATTGTG | 1320 |
| AGAAACAGGG | CCGAGCACAG | TGGCTCACGC | CTGTAATACC | AGCACCTTAG | AGGTCGAGGC | 1380 |
| AGGCGGATCA | CTTGAGGTCA | GGAGTTCAAG | ACCAGCCTGG | CCAATATGGT | GAAACCCAGT | 1440 |
| CTCTACTAAA | AATACAAAAA | TTAGCTAGGC | ATGATGGCGC | ATGCCTATAA | TCCCAGCTAC | 1500 |
| TCGAGTGCCT | GAGGCAGGAG | AATTGCATGA | ACCCGGGAGG | AGGAGGAGGA | GGTTGCAGTG | 1560 |
| AGCCGAGATA | GCGGCACTGC | ACTCCAGCCT | GGGTGACAAA | GTGAGACTCC | ATCTCAAAAA | 1620 |
| AAAAAAAAAA | AAATTGTGAG | AAACAGAAAT | ACTTAAAATG | AGGAATAAGA | ATGGAGATGT | 1680 |
| TACATCTGGT | AGATGTAACA | TTCTACCAGA | TTATGGATGG | ACTGATCTGA | AAATCGACCT | 1740 |
| CAACTCAAGG | GTGGTCAGCT | CAATGCTACA | CAGAGCACGG | ACTTTTGGAT | TCTTTGCAGT | 1800 |
| ACTTTGAATT | TATTTTTCTA | CCTATATATG | TTTTATATGC | TGCTGGTGCT | CCATTAAAGT | 1860 |
| TTTACTCTGT | GTTGC | | | | | 1875 |

(2) INFORMATION FOR SEQ ID NO:4:

(i) SEQUENCE CHARACTERISTICS:
        (A) LENGTH: 325 amino acids
        (B) TYPE: amino acid
        (C) STRANDEDNESS: single
        (D) TOPOLOGY: linear (ii) MOLECULE TYPE: protein (iii) HYPOTHETICAL: NO (v) FRAGMENT TYPE:

(xi) SEQUENCE DESCRIPTION: SEQ ID NO:4:

```
Met  Ala  Trp  Ser  Leu  Gly  Ser  Trp  Leu  Gly  Gly  Cys  Leu  Leu  Val  Ser
 1                  5                    10                       15

Ala  Leu  Gly  Met  Val  Pro  Pro  Glu  Asn  Val  Arg  Met  Asn  Ser  Val
                20                  25                      30

Asn  Phe  Lys  Asn  Ile  Leu  Gln  Trp  Glu  Ser  Pro  Ala  Phe  Ala  Lys  Gly
           35                       40                   45

Asn  Leu  Thr  Phe  Thr  Ala  Gln  Tyr  Leu  Ser  Tyr  Arg  Ile  Phe  Gln  Asp
      50                       55                      60

Lys  Cys  Met  Asn  Thr  Thr  Leu  Thr  Glu  Cys  Asp  Phe  Ser  Ser  Leu  Ser
 65                      70                      75                       80

Lys  Tyr  Gly  Asp  His  Thr  Leu  Arg  Val  Arg  Ala  Glu  Phe  Ala  Asp  Glu
                 85                      90                      95

His  Ser  Asp  Trp  Val  Asn  Ile  Thr  Phe  Cys  Pro  Val  Asp  Thr  Ile
               100                  105                     110

Ile  Gly  Pro  Pro  Gly  Met  Gln  Val  Glu  Val  Leu  Ala  Asp  Ser  Leu  His
          115                      120                     125

Met  Arg  Phe  Leu  Ala  Pro  Lys  Ile  Glu  Asn  Glu  Tyr  Glu  Thr  Trp  Thr
     130                      135                     140

Met  Lys  Asn  Val  Tyr  Asn  Ser  Trp  Thr  Tyr  Asn  Val  Gln  Tyr  Trp  Lys
145                      150                     155                      160

Asn  Gly  Thr  Asp  Glu  Lys  Phe  Gln  Ile  Thr  Pro  Gln  Tyr  Asp  Phe  Glu
                165                     170                     175
```

| | | | | | | | | | | | | | | |
|---|---|---|---|---|---|---|---|---|---|---|---|---|---|---|
| Val | Leu | Arg | Asn 180 | Leu | Glu | Pro | Trp | Thr 185 | Thr | Tyr | Cys | Val | Gln 190 | Val | Arg |
| Gly | Phe | Leu 195 | Pro | Asp | Arg | Asn | Lys 200 | Ala | Gly | Glu | Trp | Ser 205 | Glu | Pro | Val |
| Cys | Glu 210 | Gln | Thr | Thr | His | Asp 215 | Glu | Thr | Val | Pro | Ser | Trp 220 | Met | Val | Ala |
| Val 225 | Ile | Leu | Met | Ala | Ser 230 | Val | Phe | Met | Val | Cys 235 | Leu | Ala | Leu | Leu | Gly 240 |
| Cys | Phe | Ser | Leu | Leu 245 | Trp | Cys | Val | Tyr | Lys 250 | Lys | Thr | Lys | Tyr | Ala 255 | Phe |
| Ser | Pro | Arg | Asn 260 | Ser | Leu | Pro | Gln | His 265 | Leu | Lys | Glu | Phe | Leu 270 | Gly | His |
| Pro | His | His 275 | Asn | Thr | Leu | Leu | Phe 280 | Phe | Ser | Phe | Pro | Leu 285 | Ser | Asp | Glu |
| Asn | Asp 290 | Val | Phe | Asp | Lys | Leu 295 | Ser | Val | Ile | Ala | Glu 300 | Asp | Ser | Glu | Ser |
| Gly 305 | Lys | Gln | Asn | Pro | Gly 310 | Asp | Ser | Cys | Ser | Leu 315 | Gly | Thr | Pro | Pro | Gly 320 |
| Gln | Gly | Pro | Gln | Ser 325 | | | | | | | | | | | |

(2) INFORMATION FOR SEQ ID NO:5:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides"

(iii) HYPOTHETICAL: NO (xi) SEQUENCE DESCRIPTION: SEQ ID NO:5:

GCCGCAAGGC GAGAGCTGC                                                                                                        19

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides"

(iii) HYPOTHETICAL: NO (xi) SEQUENCE DESCRIPTION: SEQ ID NO:6:

AGATCTAAGC TTGGCCGAGG                                                                                                     20

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides"

(iii) HYPOTHETICAL: NO ( x i ) SEQUENCE DESCRIPTION: SEQ ID NO:7:

GCGGAATTCT TAATCACTGG GGCACAG 27

( 2 ) INFORMATION FOR SEQ ID NO:8:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( i i i ) HYPOTHETICAL: NO ( x i ) SEQUENCE DESCRIPTION: SEQ ID NO:8:

GTCCATGGCG TGGAGCCTTG GGAG 24

( 2 ) INFORMATION FOR SEQ ID NO:9:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( i i i ) HYPOTHETICAL: NO ( x i ) SEQUENCE DESCRIPTION: SEQ ID NO:9:

GATGCCTCCA CTGAGCTTCA GCAACTTTGG ATTCCAGTTG TTGC 44

( 2 ) INFORMATION FOR SEQ ID NO:10:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( i i i ) HYPOTHETICAL: NO ( x i ) SEQUENCE DESCRIPTION: SEQ ID NO:10:

GACCCTCTTT CCCAGCTGC 19

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( i i i ) HYPOTHETICAL: NO ( x i ) SEQUENCE DESCRIPTION: SEQ ID NO:11:

GCCACACATC CTCTTTACGC 20

( 2 ) INFORMATION FOR SEQ ID NO:12:

( i ) SEQUENCE CHARACTERISTICS:

( A ) LENGTH: 21 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Oligonucleotides"

( i i i ) HYPOTHETICAL: NO ( x i ) SEQUENCE DESCRIPTION: SEQ ID NO:12:

GCCTTTTTTA GTTATTATGT C    21

( 2 ) INFORMATION FOR SEQ ID NO:13:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Oligonucleotides"

( i i i ) HYPOTHETICAL: NO ( x i ) SEQUENCE DESCRIPTION: SEQ ID NO:13:

ATCGCTAGCC ATTGCTGAAG CTCAGTGGAG G    31

( 2 ) INFORMATION FOR SEQ ID NO:14:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Oligonucleotides"

( i i i ) HYPOTHETICAL: NO ( x i ) SEQUENCE DESCRIPTION: SEQ ID NO:14:

GTGGCTAGCT ATAGTTGGAA TTTGTATTGC    30

( 2 ) INFORMATION FOR SEQ ID NO:15:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Oligonucleotides"

( i i i ) HYPOTHETICAL: NO ( x i ) SEQUENCE DESCRIPTION: SEQ ID NO:15:

GTGGCTAGCA TAATTACTGT GTTTTTGAT    29

( 2 ) INFORMATION FOR SEQ ID NO:16:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Oligonucleotides"

( i i i ) HYPOTHETICAL: NO ( x i ) SEQUENCE DESCRIPTION: SEQ ID NO:16:

GTGGCTAGCC GTCATCCTCA TGGCCTCG                                       28

( 2 ) INFORMATION FOR SEQ ID NO:17:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( i i i ) HYPOTHETICAL: NO ( x i ) SEQUENCE DESCRIPTION: SEQ ID NO:17:

CGGTTCAGGA ACAATCGG                                                  18

( 2 ) INFORMATION FOR SEQ ID NO:18:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( i i i ) HYPOTHETICAL: NO ( x i ) SEQUENCE DESCRIPTION: SEQ ID NO:18:

CAAGCGCCAT GTTGAAGCC                                                 19

( 2 ) INFORMATION FOR SEQ ID NO:19:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( i i i ) HYPOTHETICAL: NO ( x i ) SEQUENCE DESCRIPTION: SEQ ID NO:19:

GTTAGTACCA CTTAGGGC                                                  18

( 2 ) INFORMATION FOR SEQ ID NO:20:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotides"

( i i i ) HYPOTHETICAL: NO ( x i ) SEQUENCE DESCRIPTION: SEQ ID NO:20:

GTGGCTAGCA TGGGAAGCCG TGGTTATC                                       28

( 2 ) INFORMATION FOR SEQ ID NO:21:

(i) SEQUENCE CHARACTERISTICS:
  (A) LENGTH: 21 amino acids
  (B) TYPE: amino acid
  (C) STRANDEDNESS: single
  (D) TOPOLOGY: linear (ii) MOLECULE TYPE: peptide (iii) HYPOTHETICAL: NO (v) FRAGMENT TYPE:

(xi) SEQUENCE DESCRIPTION: SEQ ID NO:21:

Lys Thr Leu Ile Glu Lys Glu Arg Phe Tyr Glu Ser Arg Cys Arg Pro
1               5                   10                  15
Val Thr Pro Ser Cys
            20

(2) INFORMATION FOR SEQ ID NO:22:

(i) SEQUENCE CHARACTERISTICS:
  (A) LENGTH: 20 amino acids
  (B) TYPE: amino acid
  (C) STRANDEDNESS: single
  (D) TOPOLOGY: linear (ii) MOLECULE TYPE: peptide (iii) HYPOTHETICAL: NO (v) FRAGMENT TYPE:

(xi) SEQUENCE DESCRIPTION: SEQ ID NO:22:

Asp Ser Gln Arg Lys Leu Gln Phe Tyr Glu Asp Lys His Gln Leu Pro
1               5                   10                  15
Ala Pro Lys Cys
            20

(2) INFORMATION FOR SEQ ID NO:23:

(i) SEQUENCE CHARACTERISTICS:
  (A) LENGTH: 17 amino acids
  (B) TYPE: amino acid
  (C) STRANDEDNESS: single
  (D) TOPOLOGY: linear (ii) MOLECULE TYPE: peptide (iii) HYPOTHETICAL: NO (v) FRAGMENT TYPE:

(xi) SEQUENCE DESCRIPTION: SEQ ID NO:23:

Ala Lys Leu Leu Pro Leu Asp Lys Asp Tyr Tyr Val Val Arg Glu Pro
1               5                   10                  15
Gly (2) INFORMATION FOR SEQ ID NO:24:

(i) SEQUENCE CHARACTERISTICS:
  (A) LENGTH: 22 base pairs
  (B) TYPE: nucleic acid
  (C) STRANDEDNESS: single
  (D) TOPOLOGY: linear (ii) MOLECULE TYPE: other nucleic acid
  (A) DESCRIPTION: /desc = "Oligonucleotides"

(iii) HYPOTHETICAL: NO (xi) SEQUENCE DESCRIPTION: SEQ ID NO:24:

GATCGATTTC CCCGAAATCA TG                22

(2) INFORMATION FOR SEQ ID NO:25:

(i) SEQUENCE CHARACTERISTICS:
  (A) LENGTH: 26 base pairs
  (B) TYPE: nucleic acid
  (C) STRANDEDNESS: single
  (D) TOPOLOGY: linear (ii) MOLECULE TYPE: other nucleic acid
  (A) DESCRIPTION: /desc = "Oligonucleotides"

(iii) HYPOTHETICAL: NO (xi) SEQUENCE DESCRIPTION: SEQ ID NO:25:

CGGGGTACCC AGGATGCTGC CGTGCC            26

CELLS EXPRESSING IL-10 RECEPTOR AND THE CRFB4 GENE PRODUCT, AN IL-10 RECEPTOR ACCESSORY PROTEIN

The research leading to the present invention was supported, at least in part, by United States Public Health Service Grant Nos. RO1 CA46465 from the National Cancer Institute, and Grant No. 1-RO1 AI36450 from the National Institutes of Health. Accordingly, the Government may have certain rights in the invention.

FIELD OF THE INVENTION

The present invention relates to the identification of intracellular signal transduction function for a putative cytokine receptor subunit. In particular, the invention relates to the identification of the signal transduction protein for the interleukin (IL)-10 receptor. Accordingly, the present invention relates to preparing recombinant cells that express the IL-10 receptor and the newly identified IL-10 signal transduction protein, e.g., for use in screening libraries of compounds for IL-10 agonists and antagonists; to restoring IL-10 function to cells in vivo, e.g. via gene therapy; and in addition to chimeric proteins comprising this signal transduction protein to agonize IL-10 activity.

BACKGROUND OF THE INVENTION

Cytokine Activation of Cells

Each cytokine which utilizes the Jak-Stat signal transduction pathway activates a distinct combination of members of the Jak and Stat families. Thus, either the Jaks, the Stats or both could contribute to the specificity of ligand action. The Jak-Stat signal transduction pathway was first discovered for interferon alpha (IFN-α) and interferon gamma (IFN-γ) by the complementation of mutant cell lines defective in response to IFN-γ and/or IFN-α [Velazquez et al., Cell, 70:313–322 (1992); Watling et al., Nature, 366:230–235 (1993); Müller et al., Nature, 366:129–135 (1993) and EMBO, 12:4221–4228 (1993); Darnell et al., Science, 264:1415–1421 (1994); Leung et al., Mol. Cell. Biol., 15:1312–1317 (1995)]. It has subsequently been shown that the same general pathway is activated by most cytokines and some growth factors [for review, see Ihle and Kerr, Trends Genet., 11:69–74 (1995); Taniguchi, Science, 268:251–255 (1995)]. This pathway is activated predominantly through receptors which do not possess intrinsic intracellular kinase domains and belong to the class I or class II cytokine receptor superfamily. The lack of inherent catalytic activity in these receptors is overcome through the use of receptor-associated kinases of the Janus kinase (Jak) family. Upon ligand binding, the receptor chains oligomerize allowing the associated kinases to interact and likely crossactivate each other by tyrosine phosphorylation. Subsequently, the activated Jaks directly phosphorylate the intracellular domains of the receptors on specific tyrosine residues. This phosphorylation allows the selective recruitment of SH2-domain containing proteins, particularly Stats (Signal transducers and activators of transcription), through a specific interaction between the Stat SH2 domains and the phosphotyrosines within the Stat recruitment sites on the intracellular domains of the receptor chains. These receptor-associated Stats are then rapidly phosphorylated, likely by the activated Jaks [Quelle et al., supra]. The phosphorylation of the Stats is followed by Stat dimerization, translocation to the nucleus and activation of cytokine inducible genes.

The Jak and Stat families are growing rapidly. The Jak family consists of four members so far: Jak1, Jak2, Jak3 and Tyk2 [Wilks et al., Mol. Cell. Biol., 11:2057–2065 (1991); Silvennoinen et al., Proc. Natl. Acad. Sci. USA, 90:8429–8433 (1993); Firmbach-Kraft et al., Oncogene, 5:1329–1336 (1990); Witthuhn et al., Cell, 742:27–236 (1994); Kawamura et al., Proc. Natl. Acad. Sci. USA, 91:6374–6378 (1994); for review see Ziemiecki et al., Trends Cell Biol., 4:207–212 (1994); Ihle et al., Trends in Biochemical Sciences, 19:222–227 (1994); Ihle et al., Trends Genet., 11:69–74 (1995); Ihle and Kerr, supra]. The Stat family now includes seven different members, which have been cloned: Stat1α, Stat1β, and Stats2–6 [Schindler et al., Proc. Natl. Acad. Sci. USA, 89:7836–7839 (1992); Fu et al., Proc. natl. Acad. Sci. USA, 89:7840–7843 (1992); Zhong et al., Science, 264:95–98 (1994) and Proc. Natl. Acad. Sci. USA, 91:4806–4810 (1994); Yamamoto et al., Mol. Cell. Biol., 14:4342–4349 (1994); Akira et al., Cell, 77:63–71 (1994); Wakao et al., Cell, 70:2182–2191(1994); Hou et al., Science, 265:1701–1706 (1994); International Patent Publication WO 95/08629, by Darnell et al., published Mar. 30, 1995; and International Patent Publication No. WO 93/19179, by Darnell et al., published Sep. 30, 1993] and several others, which were identified by electrophoretic mobility shift assays, but have not been cloned yet [Meyer et al., J. Biol. Chem., 269:4701–4704 (1994); Finbloom et al., Mol. Cell. Biol., 14:2113–2118 (1994); Tian et al., Blood, 84:1760–1764 (1994); Finbloom and Winestock, J. Immnol., 155:1079–1090 (1995); Frank et al., Proc. Natl. Acad. Sci. USA, 92:7779–7783 (1995)].

The Jak kinases are characterized by seven conserved domains: two PTK-related domains and five domains with unknown functions [Ziemiecki et al., supra]. The main difference between Jaks and other protein tyrosine kinases (PTK) is that along with a kinase domain, shown to be active [Wilks et al., supra], they also contain a PTK-like domain with substitutions of several residues essential for kinase activity. Thus, the second domain is expected to be inactive as a PTK and probably has some other function. Another feature of this family is the lack of any detectable SH2 or SH3 domains. The functions of the other five regions of homology are also unknown.

Stats represent proteins containing SH2, SH3 and DNA-binding domains [for reviews, see Darnell et al., supra; Fu, Journal of Leukocyte Biology, 57:529–535 (1995)]. The highly selective and specific interaction between Stat SH2 domains and the phosphotyrosine containing Stat recruitment sites on the intracellular domains of the cytokine receptors determines which Stats are to be recruited to a particular receptor complex [Heim et al., Science, 267:1347–1349 (1995); Stahl et al., Science, 267:1349–1353 (1995)].

The intracellular domain of each cytokine receptor specifically associates with one or more distinct Jaks. While some Jaks and Stats participate in several cytokine signalling pathways, others are more restricted. In the case of Jaks, Jak2 and, especially Jak1, associate with receptors participating in different apparently unrelated cytokine-receptor systems [for reviews, see Ziemiecki et al., supra; Ihle et al., supra; Taniguchi, supra; Ihle and Kerr, supra]. Jak3 appears to be restricted to the ligand receptor systems through its association with the IL-2R$\gamma_c$ chain [Johnston et al., Nature, 370:151–153 (1994); Witthuhn et al., supra; Russell et al., Science, 266:1042–1045 (1994); Miyazaki et al., Science, 266:1045–1047 (1994); Tanaka et al., Proc. Natl. Acad. Sci. USA, 91:7271–7275 (1994)]. Tyk2 was shown to be activated during IFN-α signalling [Velazquez et al., supra; Barbieri et al., Eur. J. Biochem., 223:427–435 (1994)] and also during CNTF-related cytokine signalling, albeit only in certain cell types [Stahl et al., *Science*, 263:92–95 (1994); Lütticken et al., *Science*, 262:89–92 (1994)]. Recently, the activation of Tyk2 by IL-10 and IL-12 was shown [Finbloom and Winestock, supra; Bacon et al., *J. Exp. Med.*, 181:399–404 (1995); Ho et al., *Mol. Cell. Biol.*, 15:5043–5053 (1995)]. Thus, the Jaks may contribute to the specificity of signal transduction at some level.

Interleukin-10

IL-10 is a pleiotropic cytokine that plays an important role in the regulation of immune response by controlling the functions of myeloid and lymphoid cells [reviewed in Moore et al., *Annu. Rev. Immunol*, 11:165–90 (1993)]. Distinct activities of IL-10 on $T_H1$- and $T_H2$-related immune functions suggest a possible role in controlling development of the class of an immune response. IL-10's multiple activities have been shown so far to include: the ability to inhibit macrophage activation and suppress cytokine synthesis by activated T cells and NK cells by blocking the ability of macrophages to act as antigen-presenting or costimulatory cells; and costimulation of proliferation and differentiation of B cells, mast cells, and thymocytes. IL-10 can inhibit dendritic and antigen presenting cell (APC) functions. It can also inhibit cytokine synthesis and effector functions of $T_H1$ cells.

IL-10 has distinct pathways for its activities, for example on NK cells. Thus, although both IL-4 and IL-10 inhibit IL-2 induced synthesis of IFN-γ and TNF-α by PBMC, IL-10 does not affect IL-2-induced NK or PBMC proliferation, nor does it affect IL-2-induced LAK activity. The effects of IL-10 on IFN-γ suppression are mediated by CD14+ cells (monocytes/macrophages) [Hsu et al., *Int. Immunol.* 4:563–569 (1991)].

Epstein-Barr virus encodes a homolog of IL-10, termed BCFR1 or vIL-10, that shares many of the cytokine's biological activities and may play a role in host-virus interaction [Moore et al., supra].

Based on activities observed and on some experiments done in vivo, IL-10 can be considered as a powerful suppressor of the production of inflammatory cytokines and stimulator of anti-inflammatory cytokines. The soluble IL-10 receptor chain can be considered as a potential antagonist to IL-10.

The IL-10 receptor binding chain was isolated and binds to IL-10, but surprisingly does not seem to bind vIL-10. The vIL-10 homolog does not compete effectively for IL-10 binding, although it serves to inhibit macrophage activation and stimulates B lymphocytes as does IL-10. Also, vIL-10 exhibited only a subset of the activities of IL-10, suggesting a greater complexity of the receptor [See Ho and Moore, *Therapeutic Immunology*, 1:173–185 (1994)].

The citation of any reference herein should not be construed as an admission that such reference is available as "Prior Art" to the instant application.

SUMMARY OF THE INVENTION

Advantageously, the present invention provides the elusive second chain of the interleukin (IL)-10 receptor (IL-10R). This second chain is a cytokine signal transduction molecule that supports IL-10 signal transduction and accordingly IL-10 function. In specific examples, infra, cells transfected with both the first chain of the IL-10R and the presently identified second chain, termed herein CRFB4, were able to transduce a signal in response to contact with IL-10. Control (untransfected) cells, which lack an IL-10 receptor, did not respond to IL-10.

Thus, in a first embodiment, the invention relates to a recombinant DNA molecule comprising a sequence encoding the IL-10 receptor operably associated with an expression control sequence and a sequence encoding CRFB4 operably associated with an expression control sequence. In particular, the recombinant DNA molecule encodes a CRFB4 has an amino acid sequence as depicted in SEQ ID NO:4; more particularly, the CRFB4 coding sequence has a nucleotide sequence as depicted in SEQ ID NO:3. In a specific embodiment, the expression control sequences comprise the promoter of human elongation factor 1α.

Naturally, the present invention extends to a transfected, and preferably transformed, mammalian cell that co-expresses an IL-10 receptor and a recombinant CRFB4 protein, which cell comprises an expression vector comprising a sequence encoding CRFB4 operably associated with an expression control sequence. In a specific aspect, the CRFB4 expressed in the cell has an amino acid sequence as depicted in SEQ ID NO:4. In a further aspect, the CRFB4 coding sequence with which the cell is transfected has a nucleotide sequence as depicted in SEQ ID NO:3. In a preferred embodiment, the expression control sequence of the vector transfected into the mammalian cell comprises the promoter of human elongation factor 1α.

In a further embodiment of the invention, the mammalian cell further comprises an expression vector comprising a sequence encoding IL-10 receptor, whereby IL-10 receptor is expressed. In a specific aspect, the invention provides a mammalian cell transformed with the DNA molecule comprising a sequence encoding the IL-10 receptor operably associated with an expression control sequence and a sequence encoding CRFB4 operably associated with an expression control sequence.

The present invention further provides a method for identifying a molecule effective as an agonist of IL-10. This assay of the invention involves contacting the transformed cell of the invention (that expresses a functional IL-10 receptor complex) with a molecule under consideration as an agonist of IL-10; and determining whether the molecule agonizes a functional activity of the signal transduction protein of IL-10. A molecule that agonizes a functional activity of the signal transduction protein of IL-10 is identified as effective to agonize IL-10. Preferably, the cell is contacted with a combinatorial library of molecules. In a specific embodiment, the functional activity of the signal transduction protein of the IL-10 receptor comprises activation of Stat1α or Stat3, or both.

As a corollary, the present invention provides a method for identifying a molecule effective as an antagonist of IL-10. This method for identifying an IL-10 antagonist involves contacting the transformed cell of the invention with a molecule under consideration as an antagonist of IL-10 and IL-10; and determining whether the molecule antagonizes a functional activity of the signal transduction protein of IL-1. A molecule that antagonizes a functional activity of the signal transduction protein of IL-10 is identified as effective to antagonize IL-10. Preferably, the cell is contacted with a combinatorial library of molecules. In a specific embodiment, the functional activity of the signal transduction protein of the IL-10 receptor comprises activation of Stat1α or Stat3, or both.

In another aspect, the invention provides an expression vector for transformation of host cells in an animal comprising a sequence encoding CRFB4 operably associated with an expression control sequence. In a further aspect, the expression vector encodes a CRFB4 having an amino acid sequence as depicted in SEQ ID NO:4. In further embodiments, the expression vector of the invention is selected from the group consisting of a viral expression vector, a retroviral expression vector, and a naked DNA expression vector.

The invention provides an associated method for restoring IL-10 sensitivity to a cell which expresses a dysfunctional IL-10 receptor capable of binding IL-10 but incapable of transducing a signal upon such binding, comprising transforming the cell with an expression vector as described above. Thus, the invention advantageously provides gene therapy for the treatment of a deficiency of IL-10 activity resulting from lack of a functional CRFB4 chain.

The invention also provides a method for inhibiting IL-10 activity comprising contacting cells that express a functional IL-10 receptor with an anti-sense CRFB4 nucleic acid. Naturally, the invention, since it provides the first identification of a functional activity for the CRFB4 chain, also includes a synthetic anti-sense CRFB4 nucleic acid comprising at least one phosphoester analog bond.

The invention further provides a method for identifying cells that express nucleic acids encoding a functional IL-10 receptor comprising contacting cells with an oligonucleotide which hybridizes under stringent conditions to a nucleic acid having a nucleotide sequence corresponding to or complementary to the sequence depicted in SEQ ID NO:3. In a specific embodiment, the cells are mast cells, macrophages, neotrophils, or B cells. Alternatively, the invention provides a method for identifying cells that express a functional IL-10 receptor comprising contacting cells with an antibody that specifically binds to a protein having an amino acid sequence as depicted in SEQ ID NO:4. In a specific embodiment, the cells are mast cells, macrophages, neotrophils, or B cells.

Accordingly, the present invention advantageously allows for determining whether cells in a subject contain or lack a functional IL-10 receptor complex, which naturally allows for determination of an appropriate therapeutic regimen to increase or decrease IL-10 activity. The invention advantageously sets forth a number of conditions that are associated with IL-10 activity, including those in which an increase or decrease in IL-10 activity is detrimental or beneficial. Thus, by providing means for increasing or decreasing IL-10 activity by directly affecting the activity of the CRFB4 chain of IL-10 receptor, the invention provides the ordinary skilled physician with a battery of therapeutic options for regulating immune responses.

These and other advantages of the present invention will be more completely elaborated in the following Drawings, Detailed Description of the Invention, and the non-limiting Examples.

DETAILED DESCRIPTION OF THE INVENTION

Figure 1:
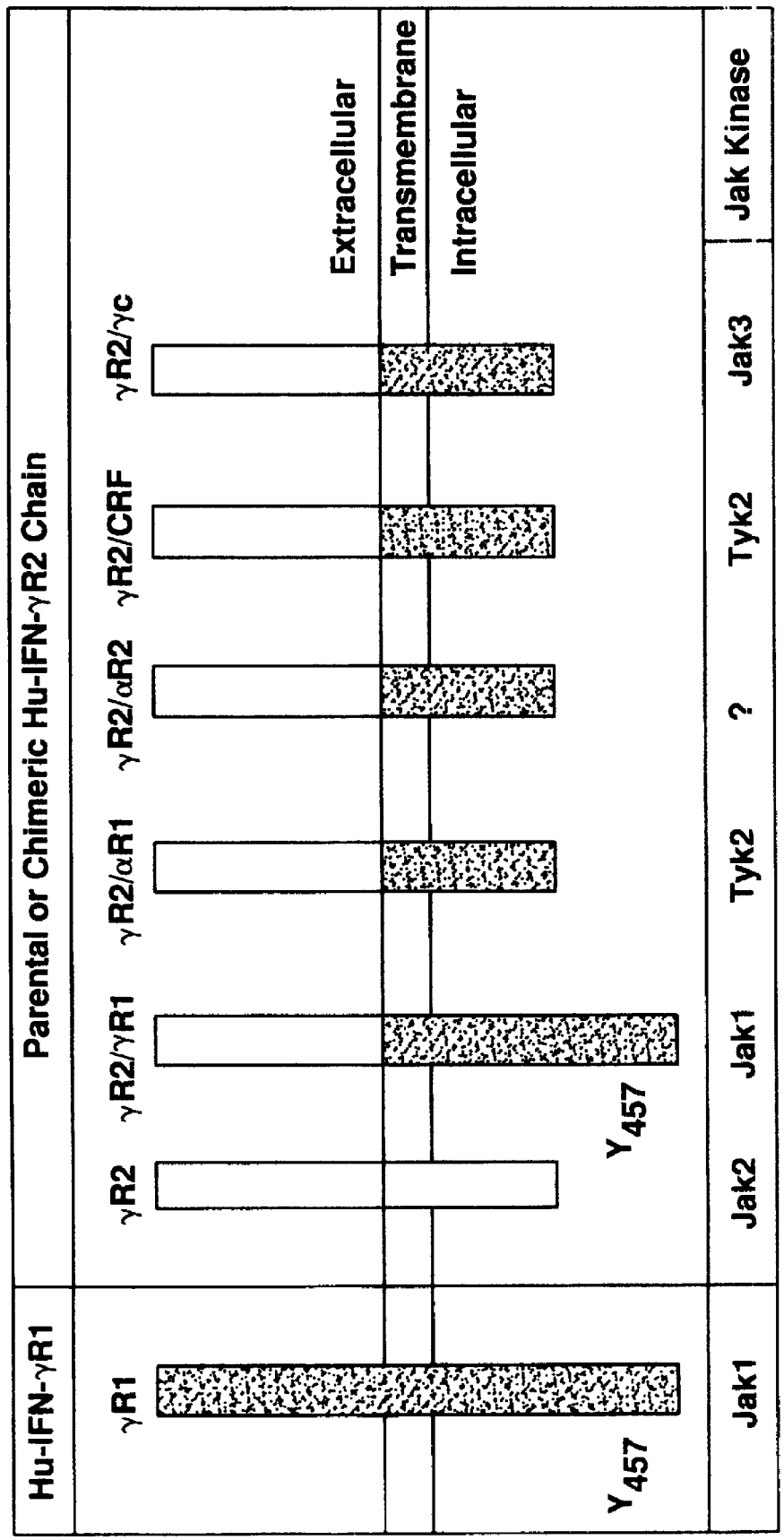
FIG. 1. Structure of Chimeric Receptors. Hu-IFN-γR1 (γR1) and Hu-IFN-γR2 (γR2) are the intact chains of the human IFN-γreceptor complex. All chimeric receptors have the extracellular domain of the human IFN-γR2 and the transmembrane and intracellular domains of different human receptors: γR2/γR1, Hu-IFN-γR1; γR2/αR1, Hu-IFN-αR1 [Uzé, et al., Cell 60:225–234 (1990)]; γR2/αR2, Hu-IFN-αR2 [Novick et al., Cell 77:381–400 (1995)]; γR2/CRF, CRFB4 [Lutfalla et al., Genomics 16:366–373 (1993)]; γR2/γ$_c$, IL-2 receptor γ$_c$ chain [Takeshita et al., Science 257:379–382 (1992)]. Although it was reported that the short form of Hu-IFN-αR2 we used binds Jak2 [Novick et al., supra], a "?" is placed under the γR1/αR2 chimera because only the long form of Hu-IFN-γR2 is functional [Lutfalla et al., EMBO J. 14:5100–8 (1995); Domanski et al., J. Biol. Chem. 270:21606–11 (1995)].

As noted above, the present invention advantageously provides the second chain of the interleukin (IL)-10 receptor (IL-10R). This second chain has been the subject of search by a number of laboratories. A gene encoding this protein was identified as a putative cytokine signal transduction molecule [Lutfalla et al., *Genomics* 16:366–373 (1993); this publication is hereby incorporated by reference in its entirety]. The present invention is based, in part, on the discovery that this chain, termed CRFB4, supports IL-10 signal transduction and accordingly IL-10 function. In specific examples, infra, cells transfected with both the first chain of the IL-10R and the presently identified second chain were able to transduce a signal in response to contact with IL-10.

Accordingly, the present invention is based, in part, on the discovery that the intracellular domain of the CRFB4 chain associates with Tyk2 tyrosine kinase. Only a few receptors use the Tyk2 molecule for signal transduction, one of which is IL-10. Thus, these data indicated that CRFB4 may be the elusive second chain of the IL-10R for which investigators have been searching. As demonstrated in the Examples, infra, transfection of cells with an expression vector containing the coding sequence (SEQ ID NO:1) for the first chain of IL-10R (SEQ ID NO:2) and the coding sequence (SEQ ID NO:3) for CRFB4 (SEQ ID NO:4) reconstituted a functionally active IL-10R complex in COS-1 cells. Treating the COS-1 cells transfected with both IL-10R and CRFB4 with human IL-10 resulted in formation of Stat-DNA binding complexes. However, cells transfected with only one or the other protein expression vector, and cells left untreated, did not form Stat-DNA complexes. Thus, the presence of IL-10R and CRFB4 is sufficient for signal transduction in response to IL-10, and the CRFB4 chain is a necessary accessory chain in the IL-10R receptor complex.

As used herein, the term "IL-10 receptor" or "IL-10R" refer to the IL-10 binding chain, which has been described [Liu et al., *J. Immunol.* 152:1821–1829 (1994); this publication is specifically incorporated herein by reference in its entirety]. The term IL-10R chain refers generally to the homologous protein from any species; preferably it is the human IL-10R chain. In a specific embodiment, the IL-10R has an amino acid sequence as depicted in SEQ ID NO:2; in a further specific embodiment, it is encoded by a cDNA having a nucleotide sequence as depicted in SEQ ID NO:1.

The term "CRFB4" as used herein refers to the polypeptide encoded by the gene mapping to the D21S58 locus identified as a member of the cytokine receptor family [Lutfalla et al., *Genomics* 16:366–373 (1993)]. The term CRFB4 chain refers generally to the homologous protein from any species; preferably it is the human CRFB4 chain. In a specific embodiment, CRFB4 has an amino acid sequence as depicted in SEQ ID NO:4; in further specific embodiment, it is encoded by a cDNA having a nucleotide sequence as depicted in SEQ ID NO:3.

The term "IL-10 receptor complex" or "IL-10R complex" refers to a protein complex comprising the foregoing IL-10R chain [Liu et al., supra] and accessory chains, in particular the CRFB4 chain which has been discovered by the present inventors as constituting the signal transduction chain of the IL-10 receptor complex. Thus, the term "components of a functional IL-10R complex" of the invention comprises the IL-10 chain and CRFB4. A "functional IL-10R complex" is capable of mediating signal transduction upon treatment with IL-10, e.g., as determined by Stat-DNA binding, which is shown in the examples infra, or other manifestations of IL-10 activity as set forth below. Various cells normally express a functional IL-10 receptor, including mast cells, macrophages, neutrophils, and B-cells. T cells also can express a functional IL-10 receptor.

The term "interleukin-10" or "IL-10" refers to the approximately 178 amino acid (including the hydrophobic leader sequence) cytokine produced by T cells, B cells, activated mast cell lines, macrophages, and keratinocytes. Human IL-10 refers to an 18-kD polypeptide lacking detectable carbohydrate. Murine IL-10 refers to a heterogeneously N-glycosylated polypeptide having apparent molecular weights of 17-, 19- and 21-kD. It has been found that glycosylation is not necessary for IL-10 biological activity. IL-10 is a potent immunosuppressant of macrophage function and cell-mediated activity; this cytokine suppresses production of inflammatory monokines such as TNF-α, IL-1, IL-6, IL-8, GM-CSF, and G-CSF by activated macrophages and monocytes, and suppresses IFN-γ production by TH1 cells. IL-10 also exerts a wide variety of immunostimulatory effects on B cells, including up-regulation of MHC class II antigen, increased B cell proliferation, and augmented differentiation of B cells into antibody-secreting cells. In addition, IL-10 augments proliferation of IL-2 and IL-4 activated T cells, mast cells, and mast cell colonies. General reviews of IL-10 and/or its receptor are given in a number of references [Bendtzen K, *Immunol. Lett.* 43:111–23 (1994); Groux et al., *Ann. NY Acad. Sci.* 770:141–8 (1995); Bromberg, *Curr. Opin. Immunol.* 7:639–43 (1995); de Vries, *Ann. Med.* 27:537–41 (1995); Mahanty and Nutman, *Parasite Immunol.* 17:385–92 (1991); Ho and Moore, *Ther. Immunol.* 1:173–85 (1994); Banchereau, *Behring Inst. Mitt.* (96):58–77 (1995); Goldman and Velu, *Adv. Nephrol. Necker Hosp.* 24:79–90 (1995)].

An "agonist" of IL-10 according to the invention is a compound that (i) binds to the IL-10 receptor; and (ii) activates signal transduction via the CRFB4 molecule, which has been newly discovered to be the signal transduction chain of the IL-10 receptor. Signal transduction by the IL-10 receptor can be evaluated in vitro by method including, but by no means limited to, (i) detecting phosphorylation of the Tyk2 tyrosine kinase; (ii) activation of Stat1$\alpha$; (iii) activation of Stat3. An IL-10 agonist is expected to have immunosuppressive activity, and thus be useful in a treatment regimen for autoimmune disease, inflammation, sepsis, and other conditions. The selective suppression of $T_H1$ immunity by IL-10 suggests use of an agonist of IL-10 to prevent allograft rejection. IL-10 enhancement of $T_H2$ immunity suggests its use as an adjuvant for vaccines where increased antibody production is desirable. In a specific embodiment, an anti-CRFB4 antibody acts as an IL-10 agonist, e.g., by promoting receptor dimerization or digomerization, or if it is an anti-idiotypic antibody.

An "antagonist" of IL-10 according to the invention is a compound that blocks IL-10 (or an IL-10 agonist) signal transduction mediated by CRFB4. In one embodiment, the antagonist competitively inhibits IL-10 binding to the IL-10 receptor. In another embodiment, the antagonist does not compete with IL-10 binding to the receptor. An IL-10 antagonist is expected to enhance immune activity, and thus be useful in antitumor responses, anti-viral responses, and in treating microbial infections, e.g., for anti-bacterial responses and anti-parasite responses, particularly intracellular pathogens. In addition, an IL-10 antagonist may reduce or eliminate transplanted organ rejection. In a specific embodiment, an anti-CRFB4 antibody acts as an IL-10 antagonist by blocking receptor activation. For example, an anti-idiotypic antibody that binds receptor but does not activate it would act as an antagonist. In another specific embodiment, a soluble CRFB4 chain, containing an IL-10 binding site but lacking its signal transduction domain, is an antagonist of IL-10.

As used herein, a "therapeutic compound" of the invention refers to an agonist or antagonist of IL-10, including synthetic oligonucleotide antisense molecules specific for CRFB4 mRNA.

Recombinant Cells That Express a Functional IL-10R Complex

According to the invention, mammalian cells may be transfected in vitro or in vitro with an expression vector or vectors that provide for expression of one or more components of a functional IL-10R complex, e.g., CRFB4, or CRFB4 and IL-10R chain. Such cells can be used in vitro for identification of agonists and antagonists of IL-10 activity, as set forth below. Alternatively, such cells can be transplanted (if not transfected in vivo) back into host animals to reconstitute IL-10 mediated functional activity. Moreover, although the examples set forth below describe co-transfection with IL-10R chain and CRFB4, the present invention further contemplates transfection with one or the other gene as necessary to reconstitute or increase the level of expression of a functional IL-10R complex.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press. (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

"Heterologous" DNA refers to DNA not naturally located in the cell, or in a chromosomal site of the cell. Preferably, the heterologous DNA includes a gene foreign to the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester anologs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6× SCC. High stringency hybridization conditions correspond to the highest $T_m$, e.g., 50% formamide, 5× or 6× SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 10 nucleotides; preferably at least about 15 nucleotides; and more preferably the length is at least about 20 nucleotides.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences. A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

As used herein, the term "sequence homology" in all its grammatical forms refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, *Cell* 50:667).

Accordingly, the term "sequence similarity" in all its grammatical forms refers to the degree of identity or correspondence between nucleic acid or amino acid sequences of proteins that do not share a common evolutionary origin (see Reeck et al., supra). However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; *DNA Cloning*, Vols. I & II, supra; *Nucleic Acid Hybridization*. supra.

Similarly, in a particular embodiment, two amino acid sequences are "substantially homologous" or "substantially similar" when greater than 30% of the amino acids are identical, or greater than about 60% are similar (functionally identical). Preferably, the similar or homologous sequences are identified by alignment using, for example, the GCG (Genetics Computer Group, *Program Manual for the GCG Package*, Version 7, Madison, Wis.) pileup program.

The term "corresponding to" is used herein to refer similar or homologous sequences, whether the exact position is identical or different from the molecule to which the similarity or homology is measured. For example, as demonstrated in FIG. 6, infra, the sequences of the DNA-binding domains of the STAT proteins can be aligned, and the corresponding amino acid residues determined, despite the deletion of amino acid residues at some positions in one STAT protein compared to another. Thus, the term "corresponding to" refers to the sequence similarity, and not the numbering of the amino acid residues or nucleotide bases.

Genes encoding IL-10R chain and CRFB4, whether genomic DNA or cDNA, can be isolated from any source, particularly from a human cDNA or genomic library. Methods for obtaining these genes are well known in the art, as described above (see, e.g., Sambrook et al., 1989, supra). Accordingly, any animal cell potentially can serve as the nucleic acid source for the molecular cloning of these genes. The DNA may be obtained by standard procedures known in the art from cloned DNA (e.g., a DNA "library"), and preferably is obtained from a cDNA library prepared from tissues with high level expression of the protein (e.g., a macrophage, T cell, or B cell cDNA library, since these are the cells that evidence highest levels of expression of functional IL-10R complex), by chemical synthesis, by cDNA cloning, or by the cloning of genomic DNA, or fragments thereof, purified from the desired cell (See, for example, Sambrook et al., 1989, supra; Glover, D. M. (ed.), 1985, *DNA Cloning: A Practical Approach*, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

The present invention also relates to genes encoding analogs and derivatives of IL-10R and CRFB4 of the invention, that have the same or homologous functional activity as the native proteins, and homologs thereof from other species. The production and use of derivatives and analogs related to these protein components of a functional IL-10R complex are within the scope of the present invention. In a specific embodiment, the derivative or analog is functionally active, i.e., capable of exhibiting one or more functional activities associated with a wild-type IL-10R complex of the invention. In another embodiment, a derivative IL-10R complex comprising the IL-10 binding domain with the CRFB4 signal transduction domain, e.g., in a chimeric protein construct, is contemplated.

IL-10R complex derivatives can be made by altering encoding nucleic acid sequences of the component proteins, e.g., IL-10R chain and CRFB4, by substitutions, additions or deletions that provide for functionally equivalent molecules. Preferably, derivatives are made that have enhanced or increased functional activity relative to native IL-10R complex.

Due to the degeneracy of nucleotide coding sequences, other DNA sequences which encode substantially the same amino acid sequence as genes for IL-10R chain and CRFB4 may be used in the practice of the present invention. These include but are not limited to allelic genes, homologous genes from other species, and nucleotide sequences comprising all or portions of the genes which are altered by the substitution of different codons that encode the same amino acid residue within the sequence, thus producing a silent change. Likewise, the IL-10R complex derivatives of the invention include, but are not limited to, those containing, as a primary amino acid sequence, all or part of the amino acid sequence of a IL-10R chain or CRFB4 protein, or both, including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred substitutions are:

Lys for Arg and vice versa such that a positive charge may be maintained;

Glu for Asp and vice versa such that a negative charge may be maintained;

Ser for Thr such that a free -OH can be maintained; and

Gln for Asn such that a free $NH_2$, can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

The genes encoding IL-10R complex derivative and analog component proteins of the invention can be produced by various methods known in the art. The manipulations which result in their production can occur at the gene or protein level. For example, the cloned gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog, care should be taken to ensure that the modified gene remains within the same translational reading frame as the native gene, uninterrupted by translational stop signals, in the gene region where the desired activity is encoded.

Additionally, a nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity of the mutated gene product. Any technique for mutagenesis known in the art can be used, including but not limited to, in vitro site-directed mutagenesis (Hutchinson, C., et al., 1978, *J. Biol. Chem.* 253:6551; Zoller and Smith, 1984, *DNA* 3:479–488; Oliphant et al., 1986, *Gene* 44:177; Hutchinson et al., 1986, *Proc. Natl. Acad. Sci. U.S.A.* 83:710), use of TAB® linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61–70).

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., *E. coli*, and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences form the yeast 2μ plasmid.

The nucleic acid, preferably DNA, molecules coding for component proteins of a functional IL-10R complex, e.g., IL-10R chain and CRFD4, or derivative or analog thereof, or a chimeric protein, thereof, can be inserted into one or more appropriate expression vector(s), i.e., a vector which contains the necessary elements for the transcription and translation of the inserted protein-coding sequence. Such elements are termed herein a "promoter." Thus, the nucleic acids encoding IL-10R chain and CRFB4 of the invention are operationally associated with a promoter in an expression vector or vectors of the invention. Both cDNA and genomic sequences can be cloned and expressed under control of such regulatory sequences. An expression vector also preferably includes a replication origin.

The necessary transcriptional and translational signals can be provided on a recombinant expression vector, or they may be supplied by the native gene encoding a IL-10R chain or CRFB4 protein and/or its flanking regions.

The expression elements of vectors vary in their strengths and specificities. Depending on the host-vector system utilized, any one of a number of suitable transcription and translation elements may be used.

The recombinant functional IL-10R complex proteins of the invention, or derivatives, chimeric constructs, or analogs thereof, may be expressed chromosomally, after integration of the coding sequence by recombination. In this regard, any of a number of amplification systems may be used to achieve high levels of stable gene expression (See Sambrook et al., 1989, supra).

The cell into which the recombinant vector or vectors comprising the nucleic acid encoding the components of the functional IL-10R complex is cultured in an appropriate cell culture medium under conditions that provide for expression of the IL-10R chain and CRFB4 proteins, and formation of a functional IL-10R complex, by the cell. In a specific embodiment, infra, the cell is an African Green Monkey kidney COS-1 cell. Other appropriate cells include, but are not limited to, chinese hamster ovary (CHO) cells; Rl.1. B—W and L—M cells; other African Green Monkey kidney cells (e.g., COS 7, BSC1, BSC40, and BMT10); murine fibroblast NIH-3T3 cells; and human cell lines such as HeLa, 2fTGH cells. HEp-2, and human kidney 293 cells; and other cells routinely used in in vitro cultures, i.e., for which optimal culture conditions have been established. In an alternative embodiment, the present invention further provides for introducing the recombinant vector or vectors that provide for expression of a functional IL-10 receptor complex into primary cells that either lack a functional receptor complex, lack expression of a functional CRFB4 protein, or that do not express IL-10 receptor.

Any of the methods for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of a IL-10R complex protein may be controlled by any promoter/enhancer element known in the art, but these regulatory elements must be functional in the host selected for expression. Promoters which may be used to control gene expression include, but are not limited to, the SV40 early promoter region (Benoist and Chambon, 1981, *Nature* 290:304–310), the promoter contained in the 3' long terminal repeat of Rous sarcoma virus (Yamamoto, et al., 1980, *Cell* 22:787–797), the herpes thymidine kinase promoter (Wagner et al., 1981, *Proc. Natl. Acad. Sci. U.S.A.* 78:1441–1445), the regulatory sequences of the metallothionein gene (Brinster et al., 1982, *Nature* 296:39–42); prokaryotic expression vectors such as the β-lactamase promoter (Villa-Kamaroff, et al., 1978, *Proc. Natl. Acad. Sci. U.S.A.* 75:3727–3731), or the tac promoter (DeBoer, et al., 1983, *Proc. Natl. Acad. Sci. U.S.A.* 80:21–25); see also "Useful proteins from recombinant bacteria" in *Scientific American*, 1980, 242:74–94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., 1984, *Cell* 38:639–646; Ornitz et al., 1986, *Cold Spring Harbor Symp. Quant. Biol.* 50:399–409; MacDonald, 1987, *Hepatology* 7:425–515); insulin gene control region which is active in pancreatic beta cells (Hanahan, 1985, *Nature* 315:115–122), immunoglobulin gene control region which is active in lymphoid cells (Grosschedl et al., 1984, *Cell* 38:647–658; Adames et al., 1985, *Nature* 318:533–538: Alexander et al., 1987, *Mol. Cell. Biol.* 7:1436–1444), mouse mammary tumor virus control region which is active in testicular, breast, lymphoid and mast cells (Leder et al., 1986, *Cell* 45:485–495), albumin gene control region which is active in liver (Pinkert et al., 1987, *Genes and Devel.* 1:268–276), alpha-fetoprotein gene control region which is active in liver (Krumlauf et al., 1985, *Mol. Cell. Biol.* 5:1639–1648; Hammer et al., 1987, Science 235:53–58), alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94), myelin basic protein gene control region which is active in oligo- dendrocyte cells in the brain (Readhead et al., 1987, Cell 48:703–712), myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378). In a specific embodiment, infra, the genes encoding both IL-10R chain and CRFB4 are under control of the powerful promoter of human elongation factor 1α [Mizushima and Nagata, Nucl. Acids Res. 18:5322 (1990)].

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; see Kaufman, Current Protocols in Molecular Biology, 16.12 (1991). Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive RSV-LTR promoter, hygromycin selectable marker; Invitrogen), pCEP4 (BamH1, SfiI, XhoI, NotI, NheI, HindIII, NheI, PvuII, and KpnI cloning site, consti- tutive hCMV immediate early gene, hygromycin selectable marker; Invitrogen), pMEP4 (KpnI, PvuI, NheI, HindIII, NotI, XhoI, SfiI, BamH1 cloning site, inducible methal- lothionein IIa gene promoter, hygromycin selectable marker: Invitrogen), pREP8 (BamH1, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEB- VHis (RSV-LTR promoter, hygromycin selectable marker, N-terminal peptide purifiable via ProBond resin and cleaved by enterokinase; Invitrogen). Selectable mammalian expres- sion vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufman, 1991, supra) for use according to the invention include but are not limited to pSC11 (SmaI cloning site, TK- and β-gal selection), pMJ601 (SalI, SmaI, AflI, NarI, BspMII, BamHI, ApaI, NheI, SacII, KpnI, and HindIII cloning site; TK- and β-gal selection), and pTKgptF1S (EcoRI, PstI, SalI, AccI, HindII, SbaI, BamHI, and Hpa cloning site, TK or XPRT selection).

In a specific embodiment, a phosphorylatable form of the CRFBA protein can be expressed [See European Patent No. 0372707 by Sidney Pestka], e.g., by using plasmid pGEX- TTK (Pharmacia, product no. 27-45-8701).

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their deriva- tives: human or animal viruses such as vaccinia virus or adenovirus; and plasmid and cosmid DNA vectors, to name but a few.

In addition, a host cell strain may be chosen which modulates the expression of the inserted sequences, or modifies and processes the gene product in the specific fashion desired. Different host cells have characteristic and specific mechanisms for the translational and post- translational processing and modification (e.g., glycosylation, cleavage [e.g., of signal sequence]) of pro- teins. Appropriate cell lines or host systems can be chosen to ensure the desired modification and processing of the foreign protein expressed. Expression in eukaryotic cells can increase the likelihood of "native" glycosylation and folding of a heterologous protein. Moreover, expression in mam- malian cells can provide a tool for reconstituting, or constituting, IL-10R complex activity. Furthermore, differ- ent vector/host expression systems may affect processing reactions, such as proteolytic cleavages, to a different extent.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

Gene Therapy and Transgenic Vectors

In one embodiment, a gene encoding a CRFB4 protein is introduced in vivo in a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infec- tive after introduction into a cell. Use of defective viral vectors allows for administration to cells in a specific, localized area, without concern that the vector can infect other cells. Thus, adipose tissue can be specifically targeted. Examples of particular vectors include, but are not limited to, a defective herpes virus 1 (HSV1) vector [Kaplitt et al., Molec. Cell. Neurosci. 2:320–330 (1991)], an attenuated adenovirus vector, such as the vector described by Stratford- Perricaudet et al. [J. Clin. Invest. 90:626–630 (1992)], and a defective adeno-associated virus vector [Samulski et al., J. Virol. 61:3096–3101 (1987); Samulski et al., J. Virol. 63:3822–3828 (1989)].

Preferably, for in vitro administration, an appropriate immunosuppressive treatment is employed in conjunction with the viral vector, e.g., adenovirus vector, to avoid immunodeactivation of the viral vector and transfected cells. For example, immunosuppressive cytokines, such as interleukin-12 (IL-12), interferon-γ (IFN-γ), interleukin-10 (IL-10), or anti-CD4 antibody, can be administered to block humoral or cellular immune responses to the viral vectors [see, e.g., Wilson, Nature Medicine (1995)]. In a further embodiment, the vector can be engineered to express such immunosuppressive cytokines. In addition, it is advanta- geous to employ a viral vector that is engineered to express a minimal number of antigens.

In another embodiment the gene can be introduced in a retroviral vector, e.g., as described in Anderson et al., U.S.

Pat. No. 5,399,346; Mann et al., *Cell* 33:153 (1983); Temin et al., U.S. Pat. No. 4,650,764; Temin et al., U.S. Pat. No. 4,980,289; Markowitz et al., *J. Virol.* 62:1120 (1988); Temin et al., U.S. Pat. No. 5,124,263; International Patent Publication No. WO 95/07358, published Mar. 16, 1995, by Dougherty et al.; and Kuo et al., *Blood* 82:845 (1993).

Targeted gene delivery is described in International Patent Publication WO 95/28494, published October 1995.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker [Felgner, et. al., *Proc. Natl. Acad. Sci. U.S.A.* 84:7413–7417 (1987); see Mackey, et al., *Proc. Natl. Acad. Sci. U.S.A.* 85:8027–8031 (1988)]. The use of cationic lipids may promote encapsulation of negatively charged nucleic acids, and also promote fusion with negatively charged cell membranes [Felgner and Ringold, *Science* 337:387–388 (1989)]. The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancreas, liver, kidney, and the brain. Lipids may be chemically coupled to other molecules for the purpose of targeting [see Mackey, et. al., supra]. Targeted peptides, e.g., hormones or neurotransmitters, and proteins such as antibodies, or non-peptide molecules could be coupled to liposomes chemically.

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter [see, e.g., Wu et al., *J. Biol. Chem.* 267:963–967 (1992); Wu and Wu, *J. Biol. Chem.* 263:14621–14624 (1988); Hartmut et al., Canadian Patent Application No. 2,012,311, filed Mar. 15, 1990].

In a further embodiment, the present invention provides a transgenic or gene therapy vector for co-expression of CRFB4 and IL-10R chain. In one embodiment, these elements are provided on separate vectors, e.g., as exemplified infra. These elements may be provided in a single expression vector.

The present invention extends to the preparation of antisense nucleotides and ribozymes that may be used to interfere with the expression of CRFB4 at the translational level. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule [see Marcus-Sekura, *Anal. Biochem.* 172:298 (1988)]. In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into organ cells. Antisense methods have been used to inhibit the expression of many genes in vitro [Marcus-Sekura, 1988, supra; Hambor et al., *J. Exp. Med.* 168:1237 (1988)]. Preferably synthetic antisense nucleotides contain phosphoester analogs, such as phosphorothiolates, or thioesters, rather than natural phosphoester bonds. Such phosphoester bond analogs are more resistant to degradation, increasing the stability, and therefore the efficacy, of the antisense nucleic acids.

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it [Cech, *J. Am. Med. Assoc.* 260:3030 (1988)]. Because they are sequence-specific, only mRNAs with particular sequences are inactivated.

Investigators have identified two types of ribozymes, Tetrahymena-type and "hammerhead"-type. Tetrahymena-type ribozymes recognize four-base sequences, while "hammerhead"-type recognize eleven- to eighteen-base sequences. The longer the recognition sequence, the more likely it is to occur exclusively in the target MRNA species. Therefore, hammerhead-type ribozymes are preferable to Tetrahymena-type ribozymes for inactivating a specific mRNA species, and eighteen base recognition sequences are preferable to shorter recognition sequences.

The DNA sequences encoding CRFB4 described and enabled herein may thus be used to prepare expression vectors, particularly transgenic and gene therapy expression vectors as described above, that express antisense molecules against or ribozymes that cleave mRNAs for CRFB4. Alternatively, the CRFB4 sequence can be used to design a synthetic antisense nucleic acid molecule, preferably comprising one or more phosphoester analog bonds. These CRFB4 mRNA-specific antisense or ribozyme molecules would inhibit translation of the mRNA encoding CRFB4, which may reduce the IL-10 mediated cellular activation. Thus, the antisense and ribozymes of the invention specific for CRFB4 can be used as antagonists of IL-10 activity.

Antibodies to CRFB4

According to the invention, CRFB4 polypeptide produced recombinantly or by chemical synthesis, and fragments or other derivatives or analogs thereof, including fusion proteins, may be used as an immunogen to generate antibodies that recognize the CRFB4 polypeptide. Such antibodies include but are not limited to polyclonal, monoclonal, chimeric, single chain, Fab fragments, and an Fab expression library. The anti-CRFB4 antibodies of the invention may be cross reactive, e.g., they may recognize CRFB4 from different species. Polyclonal antibodies have greater likelihood of cross reactivity. Alternatively, an antibody of the invention may be specific for a single form of CRFB4, such as murine CRFB4. Preferably, such an antibody is specific for human CRFB4.

Various procedures known in the art may be used for the production of polyclonal antibodies to CRFB4 polypeptide or derivative or analog thereof. For the production of antibody, various host animals can be immunized by injection with the CRFB4 polypeptide, or a derivative (e.g., fragment or fusion protein) thereof, including but not limited to rabbits, mice, rats, sheep, goats, etc. In one embodiment, the CRFB4 polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the CRFB4 polypeptide, or fragment, analog, or derivative thereof, any technique that provides for the production of antibody molecules by continuous cell lines in culture may be used. These include but are not limited to the hybridoma technique originally developed by Kohler and Milstein [*Nature* 256:495–497 (1975)], as well as the trioma technique, the human B-cell hybridoma technique [Kozbor et al., *Immunology Today* 4:72 1983); Cote et al., *Proc. Natl. Acad. Sci. U.S.A.* 80:2026–2030 (1983)], and the EBV-hybridoma technique to produce human monoclonal antibodies [Cole et al., in *Monoclonal Antibodies and Cancer Therapy*, Alan R. Liss, Inc., pp. 77–96 (1985)]. In an additional embodiment of the invention, monoclonal antibodies can be produced in germ-free animals utilizing recent technology [PCT/US90/02545]. In fact, according to the invention, techniques developed for the production of "chimeric antibodies" [Morrison et al., *J. Bacteriol.* 159:870 (1984); Neuberger et al., *Nature* 312:604–608 (1984); Takeda et al., *Nature* 314:452–454 (1985)] by splicing the genes from a mouse antibody molecule specific for an CRFB4 polypeptide together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies [U.S. Pat. No. 4,946, 778] can be adapted to produce CRFB4 polypeptide-specific single chain antibodies. An additional embodiment of the invention utilizes the techniques described for the construction of Fab expression libraries [Huse et al., *Science* 246:1275–1281 (1989)] to allow rapid and easy identification of monoclonal Fab fragments with the desired specificity for an CRFB4 polypeptide, or its derivatives, or analogs.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of an CRFB4 polypeptide, one may assay generated hybridomas for a product which binds to an CRFB4 polypeptide fragment containing such epitope. For selection of an antibody specific to a CRFB4 polypeptide from a particular species of animal, one can select on the basis of positive binding with CRFB4 polypeptide expressed by or isolated from cells of that species of animal, and negative binding with CRFB4 from other species.

The foregoing antibodies can be used in methods known in the art relating to the localization and activity of the CRFB4 polypeptide, e.g., for Western blotting, imaging CRFB4 polypeptide in situ, measuring levels thereof in appropriate physiological samples, etc., using any of the detection techniques mentioned above or known in the art.

In a specific embodiment, antibodies that agonize or antagonize the activity of CRFB4 polypeptide can be generated. Such antibodies can be tested using the assays described infra for identifying ligands.

Identification of IL-10 Receptor Ligands: Agonists and Antagonists

The identification of CRFB4 as the signal transduction chain for the IL-10 receptor provides for expression of the functional receptor in cells engineered to indicate the activity of the IL-10 receptor expressed after transfection or transduction of the cells. Accordingly, the present invention contemplates a method for identifying specific ligands of the IL-10 receptor, and more particularly ligands that both agonize and antagonize receptor activity, using various screening assays known in the art.

Any screening technique known in the art can be used to screen for IL-10 agonists or antagonists. The present invention contemplates screens for small molecule ligands or ligand analogs and mimics, as well as screens for natural ligands that bind to and agonize or antagonize IL-10 in vivo. For example, natural products libraries can be screened using assays of the invention for molecules that agonize or antagonize IL-10 activity. In addition, screening for anti-idiotypic antibodies, e.g., based on competitive binding with IL-10 to CRFB4, can be used to identify anti-idiotypic agonists and antagonists.

Another approach to screening for biologically active compounds uses recombinant bacteriophage to produce large libraries. Using the "phage method" [Scott and Smith, 1990, *Science* 249:386–390 (1990); Cwirla, et al., *Proc. Natl. Acad. Sci.*, 87:6378–6382 (1990); Devlin et al., *Science*, 249:404–406 (1990)], very large libraries can be constructed ($10^6$–$10^8$ chemical entities). A second approach uses primarily chemical methods, of which the Geysen method [Geysen et al., *Molecular Immunology* 23:709–715 (1986); Geysen et al. *J. Immunologic Method* 102:259–274 (1987)] and the method of Fodor et al. [*Science* 251:767–773 (1991)] are examples. Furka et al. [14*th International Congress of Biochemistry*, Volume 5, Abstract FR:013 (1988); Furka, *Int. J. Peptide Protein Res.*

37:487–493 (1991)], Houghton [U.S. Pat. No. 4,631,211, issued December 1986] and Rutter et al. [U.S. Pat. No. 5,010,175, issued Apr. 23, 1991] describe methods to produce a mixture of peptides that can be tested as agonists or antagonists.

In another aspect, synthetic libraries [Needels et al., Proc. Natl. Acad. Sci. USA 90:10700–4 (1993): Ohlmeyer et al., Proc. Natl. Acad. Sci. USA 90:10922–10926 (1993); Lam et al., International Patent Publication No. WO 92/00252; Kocis et al., International Patent Publication No. WO 9428028, each of which is incorporated herein by reference in its entirety], and the like can be used to screen for IL-10 receptor ligands according to the present invention.

Various assays may be performed to determine whether the candidate molecule, e.g., prepared in a combinatorial library as described above, or found in a library of natural products, acts as an agonist or antagonist of IL-10. In a preferred embodiment, these tests employ recombinant cells engineered to express a functional IL-10 receptor complex comprising the IL-10R chain and CRFB4 as described above. In a specific embodiment, an assay of the invention employs COS-1 cells transfected with vectors that provide for expression of IL-10R chain and CRFB4.

Detection of IL-10 receptor-mediated activation (or inhibition of activation) can be accomplished by evaluating changes in cell targets, preferably transfected cells as described above. CRFB4-mediated activation can be detected and quantified (or semi-quantified) by detecting increased phosphorylation of Tyk2, activation of Stat1 or Stat3, decreased production of interferon-γ, etc.

As shown in a specific embodiment, infra, phosphorylation of Tyk2 can be measured by double immunoprecipitation assays with an anti-Tyk2 antibody and an anti-phosphoprotein antibody, and detection of an identical band in both precipitations. Alternatively, Tyk2 phosphorylation can be evaluated by co-transfection of cells transfected with IL-10R and CRFB4 with a vector for expression of Tyk2, and detection of phosphorylation by gel shift, antibody probes, or radiolabelling with $^{32}$P.

Activation of Stat proteins can be evaluated by any of the techniques described in International Patent Publication No. WO 95/08629, by Darnell et al., published Mar. 30, 1995, and International Patent Publication No. WO 93/19179, by Darnell et al., published Sep. 30, 1993. In specific embodiments, Stat protein activation can be evaluated by detecting Stat1 dimerization, or in gel-shift electrophoretic mobility shift assays (EMSA) using binding sites. For example, a 22 base pair sequence containing a Stat1α binding site corresponding to the GAS element in the promoter region of the human IRF-1 gene can be used to evaluate Stat1 α activation [see Kotenko et al., J. Biol. Chem. 270:20915–21 (1995)].

Interferon-γ expression can be detected using biological assays, e.g., antiviral assays, or immunometrically, such as by ELISA, ELISPOT, immunoprecipitation, etc.

An agonist of IL-10 will lead to positive results in the foregoing assays, e.g., and increase in the level of Tyk2 activation, increased Stat1 and Stat3 activation, and increased IFN-γ expression. Conversely, an antagonist of IL-10 will suppress these activities in the presence of IL-10. Thus, in an assay of the invention for an agonist of IL-10, increased activation will indicate that a candidate molecule is an agonist. In an assay of the invention for an antagonist of IL-10, inhibition of activation in the presence of IL-10 will indicate that a candidate molecule is an antagonist.

It should be noted that in a specific embodiment, an anti-CRFB4 antibody can act as an IL-10 agonist, by binding to CRFB4 in such a way as to mimic the action of IL-10 binding to the IL-10 receptor complex. The present invention contemplates using the foregoing methods to select such agonist antibodies.

Similarly, an anti-CRFB4 antibody can act as an IL-10 antagonist, by binding to CRFB4 in such a way as to prevent its productive interaction in the IL-10 receptor complex, or via other mechanisms. As with antibody agonists of IL-10, an antibody antagonist can be selected using the methods described above.

Diagnostics

The antibodies or nucleic acids of the invention can be used in diagnosis of diseases or disorders associated with apparent defects in IL-10 activity by evaluating the level of expression of a functional IL-10 receptor complex. In particular, nucleic acid probes or PCR primers can be used to verify expression of mRNA coding for CRFB4 in standard Northern or RT-PCR analysis. The absence of detection of mRNA in cells from a subject that appears to lack sufficient IL-10 activity would indicate that the deficiency lies with a non-functional receptor. Similarly, anti-CRFB4 antibodies can be used to detect expression of a CRFB4 protein in cells, and in some instances, to localize the expression to the cell surface. The absence of immunodetection of CRFB4 would also indicate that the deficiency lies with a non-functional IL-10 receptor complex. Such a subject is strongly indicated for gene therapy, to restore IL-10 activity by transfecting the cells with the functional IL-10 receptor complex signal transduction chain.

In specific embodiments, a deficiency in CRFB4 activity may be evaluated in the context of a disease or disorder associated with suppression of IL-10 activity, including but not limited to photosensitivity, inflammation, autoimmunity, septic shock, autologous organ transplantation rejection, and similar conditions associated with disregulated increased immune response.

Increased expression or activity of the CRFB4 chain of the IL-10 receptor complex may be evaluated by a number of criteria, such as quantitative immunoassay, or observation of signalling in the absence of IL-10, or in the presence of an IL-10 antagonist such as an anti-IL-10 antibody or soluble IL-10 binding domain of the IL-10R chain. Detection of these conditions would indicate treatment to inhibit CRFB4-mediated cellular activation, e.g., by blocking CRFB4 expression with antisense or ribozyme technology, using an inhibitory (antagonist) antibody, or by selecting an IL-10 antagonists of the invention that is selected or tested for the ability to block the inappropriate signalling activity.

In specific embodiments, increased IL-10 receptor activity can be detected in the context of diseases or disorders associated with excessive immunosuppression, such as but not limited to, tumors, viral infections, bacterial or parasitic infections, particularly those associated with intracellular pathogens.

Therapeutics

As noted above, the present invention provides for increasing or decreasing the activity of IL-10, i.e., agonizing or antagonizing the important regulatory roles played by IL-10 where such would benefit a subject. These methods can be accomplished by (i) transfecting cells with functional CRFB4, or CRFB4 and IL-10R chain, to reconstitute or establish a functional IL-10 receptor complex; (ii) transfecting cells with a CRFB4 mRNA-specific antisense or ribozyme gene, or introducing a synthetic antisense molecule, to suppress expression of CRFB4 and expression of a functional IL-10 receptor complex; (iii) introducing a small molecule IL-10 agonist or antagonist identified according to the invention to a subject in need of such treatment; and (iv) contacting cells with an anti-CRFB4 antibody that agonizes or antagonizes IL-10 activity.

Imbalance towards $T_H1$ predominance is associated with acceleration of lupus-like autoimmune syndrome in MRL mice. As discussed above, IL-10 suppresses $T_H1$ cells. Therefore, an agonist of IL-10 is expected able to inhibit this and other autoimmune syndromes [Takahashi et al., *J. Clin. Invest.* 97:1597–604 (1996)]. As $T_H2$ cells mediate UVB-induced suppression of contact photosensitivity by releasing IL-10, [Yagi et al., *J. Immunol.* 156:1824–31 (1996)], an agonist of IL-10 would be expected to suppress contact photosensitivity. In another embodiment, agonists of IL-10 would suppress inflammatory cytokines [Marietta et al., *Eur. J. Immunol.* 26:49–56 (1996); Ertel et al., *Arch. Surg.* 131:51–6 (1996)] in rheumatoid arthritis [Sugiyama et al., *J. Rheumatol.* 22:2020–6 (1995)] and could assist in stimulation of erythopoiesis [Wang et al., *J. Cell. Physiol.* 166:305–10 (1996)]. More generally, an agonist of IL-10 may demonstrate immunosuppressive and anti-inflammatory properties [de Vries, *Ann. Med.* 27:537–41 (1995); Buelens et al., *Adv. Exp. Med. Biol.* 378:363–5 (1995); Hancock et al., *Am. J. Pathol.* 147:1193–9 (1995)]. Staphylococcal enterotoxin B and tumor-necrosis factor-alpha (TNF-α) induced relapses of experimental allergic encephalomyelitis that could be blocked by transforming growth factor-beta and IL-10 [Crisi et al., *Eur. J. Immunol.* 25:3035–40 (1995)].

The selective suppression of $T_H1$, immunity by IL-10 suggests the use of IL-10 in preventing allograft rejection. IL-10's enhancement of $T_H2$ immunity suggests the use of IL-10 as an adjuvant for vaccines where enhanced antibody production is desired.

Antagonists of IL-10 may selectively enhance $T_H1$ immunity, which would be of benefit in infectious diseases of viral origin or in those involving bacteria or parasites that are intracellular pathogens. The antagonists might be candidates for the treatment of B cell mediated autoimmune diseases such as septic endotoxin shock by selectively enhancing $T_H1$ immunity.

A number of studies indicate that an antagonist of IL-10 should enhance antitumor responses of the immune system. Production of IL-10 by some types of tumors may prevent an adequate immune response against the transformed cells, and the antagonists may be used in such situations. For example, an inhibitor of the IL-10 receptor may help treat chronic B-lymphocytic leukemia because IL-10 was reported to prevent leukemic cells from apoptotic cell death [Kitabayashi et al., *Int. J. Hematol.* 62:99–106 (1995)]. In addition, human IL-10 was reported to inhibit antitumor immune responses in vitro [Hishii et al., *Neurosurgery* 37:1160–7 (1995)]. Furthermore, the presence of Epstein-Barr virus interleukin-10 was found in the serum of patients with diffuse large-cell non-Hodgkin's lymphomas [Blay et al., *Blood* 86:4702–4 (1995)]. CD8 T cell clones were reported to inhibit antitumor T cell function by secreting IL-10 [Rohrer and Coggin, *J. Immunol.* 155:5719–27 (1995)]. Selective expression of IL-10 mRNA was reported in human renal cell carcinoma [Panuska et al., *J. Clin. Invest.* 96:2445–53 (1995)].

Blocking the IL-10 receptor would enhance the production of IFN-γ required for an effective response against many microbial infections. Thus, antagonists of IL-10 would enhance antilisterial activity of human blood-derived macrophages by permitting increased production of IFN-γ [Blauer et al., *J. Interferon Cytokine Res.* 15:105–14 (1995); Krishnan et al., *J. Immunol.* 156:653–62 (1996). Similarly, IL-10R antagonists would assist in eliminating Yersinia enterocolitica infections [Bohn and Autenrieth, *J. Immunol.* 156:1458–68 (1996)].

According to the invention, the component or components of a therapeutic composition of the invention, i.e., an agonist or antagonist of IL-10 identified according to the invention, may be introduced parenterally, transmucosally, e.g., orally, nasally, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration. More preferably, where administration of an antagonist of IL-10 is indicated to induce immunological activity toward a tumor, or alternatively where administration of an agonist of IL-10 is indicated to suppress rejection of an allograft, it may be introduced by injection into the tumor (or allograft) or into tissues surrounding the tumor (or allograft).

In another embodiment, the therapeutic compound can be delivered in a vesicle, in particular a liposome [see Langer, *Science* 249:1527–1533 (1990); Treat et al., in *Liposomes in the Therapy of Infectious Disease and Cancer*, Lopez-Berestein and Fidler (eds.), Liss: N.Y., pp. 353–365 (1989); Lopez-Berestein, ibid., pp. 317–327; see generally ibid.].

In yet another embodiment, the therapeutic compound can be delivered in a controlled release system. For example, the polypeptide may be administered using intravenous infusion, an implantable osmotic pump, a transdermal patch, liposomes, or other modes of administration. In one embodiment, a pump may be used [see Langer, supra; Sefton, *CRC Crit. Ref. Biomed. Eng.* 14:201 (1987); Buchwald et al., *Surgery* 88:507 (1980); Saudek et al., *N. Engl. J. Med.* 321:574 (1989)]. In another embodiment, polymeric materials can be used [see *Medical Applications of Controlled Release*, Langer and Wise (eds.), CRC Press: Boca Raton, Fla. (1974); *Controlled Drug Bioavailability, Drug Product Design and Performance*, Smolen and Ball (eds.), Wiley: N.Y. (1984); Ranger and Peppas, *J. Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)]. In yet another embodiment, a controlled release system can be placed in proximity of the therapeutic target, i.e., the brain, thus requiring only a fraction of the systemic dose [see, e.g., Goodson, in *Medical Applications of Controlled Release, supra*, vol. 2, pp. 115–138 (1984)]. Preferably, a controlled release device is introduced into a subject in proximity of the site of inappropriate immune activation or a tumor. Other controlled release systems are discussed in the review by Langer [*Science* 249:1527–1533 (1990)].

Thus, the agonist or antagonist of IL-10 can be delivered by intravenous, intraarterial, intraperitoneal, intramuscular, or subcutaneous routes of administration. Alternatively, the therapeutic compound, properly formulated, can be administered by nasal or oral administration. A therapeutically effective dose (i.e., a dose effective to induce metabolic changes in a subject) can be provided at the necessary intervals, e.g., daily, every 12 hours, etc. These parameters will depend on the severity of the disease condition being treated, other actions, such as diet modification, that are implemented, the weight, age, and sex of the subject, and other criteria, which can be readily determined according to standard good medical practice by those of skill in the art.

A subject in whom administration of a therapeutic compound of the invention is an effective therapeutic regiment is preferably a human, but can be any animal. Thus, as can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological park), research animals, such as mice, rats, rabbits, goats, sheep, pigs, dogs, cats, etc., avian species, such as chickens, turkeys, songbirds, etc., i.e., for veterinary medical use.

The present invention may be better understood by reference to the following non-limiting Examples, which are provided as exemplary of the invention.

EXAMPLES

Example 1

Signalling by IFN-γ With Chimeric IFN-γR2 Chain Containing Intracellular Domains From Various Receptors To assess whether the specificity of signal transduction resides in the Jaks, a variety of chimeric receptors based on the human IFN-γ receptor complex were prepared. The extracellular domain of the second human IFN-γ receptor chain, designated Hu-IFN-γR2 or AF-1 [Soh et al., *J. Biol. Chem.*, 269:18102–18110 (1994)], was fused to the transmembrane and intracellular domains of various receptors. Notably, this receptor was fused to a signal transduction chain of previously unknown function. The present Example provides evidence that this cytokine signal transduction chain of unknown function is the signal transduction chain for the IL-10 receptor.

Materials and Methods

Reagents, Restriction Endonucleases and Other Enzymes. Taq polymerase and all restriction endonucleases were from Boehringer Mannheim Biochemicals or New England Biolabs; Sequenase 2.0 and T4 DNA ligase were from United States Biochemical Corporation. The [α-$^{32}$P]dATP and [γ-$^{32}$P]ATP were from New England Nuclear. The crosslinker bis(sulfosuccinimidyl)suberate (BS$^3$) was from Pierce Chemical Co. All other chemical reagents were analytical grade and purchased from United States Biochemical Corp.

Plasmid Construction. The vector pγR2 expressing the Hu-IFN-γR2 chain under control of CMV promoter was constructed as described previously [Soh et al., *Cell*, 76:793–802 (1994); Kotenko et al., *J. Biol. Chem.*, 270:20915–20921 (1995)]. The vector pγR1 expressing the Hu-IFN-γR1 chain was constructed as follows. The pHu-IFN-γR8 plasmid [Kumar et al., *J. Biol. Chem.*, 264:17939–17946 (1989)] was digested with HindIII restriction endonuclease, incubated with the large fragment of DNA polymerase I and dNTPs to fill in the ends and then digested with BamHI restriction endonuclease. The fragment containing the Hu-IFN-γR1 cDNA was ligated into EcoRV and BamHI sites of the pcDNA3 vector (Invitrogen).

The Hu-IFN-αR1 cDNA was recloned from HuIFNAR1/pcDNAI [Lim, Ph.D. Thesis, Rutgers University, Piscataway, N.J., (1995)] into pcDNA3 with EcoRI and XbaI restriction endonucleases. The expression vector was designated pαR1. The PCR products for Hu-IFN-γR2 cDNA were obtained by a nested PCR procedure with a λpCEV15 phage DNA mixture isolated from about 5×10$^6$ phage clones from the human M426 cell library [Miki et al., *Gene*, 83:137–146 (1989)] as template. The primers for the first round of PCR were: 5'-GCCGCAAGGCGAGAGCTGC-3' (SEQ ID NO:5) specific for the 5' end of Hu-IFN-αR2 cDNA [Novick et al., *Cell*, 77:391–400 (1995)]; and λpCEV15 vector primer 5'-AGATCTAAGCTTGGCCGAGG-3' (SEQ ID NO:6). For the second round the same 5' primer and primer 5'-GCGGAATTCTTAATCACTGGGGCACAG-3' (SEQ ID NO:7) specific for the 3' end (bases 1204–1222) of Hu-IFN-αR2 cDNA (boldface) containing an EcoRI site within the primer were used. The PCR product was digested with EcoRI restriction endonuclease and ligated into EcoRI and blunt ended BamHI sites of the pcDNA3 vector. The expression vector was designated pαR2.

To isolate the Hu-CRFB4 cDNA an oligonucleotide 5'-GTCCATGGCGTGGAGCCTTGGGAG-3' (SEQ ID NO:8) homologous to the 5' end of Hu-CRFB4 cDNA [Lutfalla et al., *Genomics*, 16:366–373 (1993)] was labeled with [α-$^{32}$P]dATP with terminal deoxynucleotide transferase to a specific activity of 5 ×10$^6$ cpm/μg. It was used to screen about 10$^6$ phages from the human M426 cell library [Miki et al., supra]. Two positive clones were purified and plasmids were rescued from these two λ phages. The CRFB4 cDNA was released from one of the rescued plasmids designated pCEV15-CRFB4-1 by digestion with ThaI and SalI restriction endonucleases and cloned into EcoRV and XhoI sites of the pcDNAIneo vector (Invitrogen). The expression vector for the Hu-CRFB4 chain was designated pCRF.

The vector expressing the chimeric receptor Hu-IFN-γR2/Hu-IFN-γR1 (γR2/γR1) was constructed as followed. The asymmetric PCR reaction was performed with a specific primer 5'-GATGCCTCCACTGAGCTTCAGCAACTTTGGATT-CCAGTTGTTGC-3' (SEQ ID NO:9) and 100-fold excess of T7 primer with plasmids pHu-IFN-γR8 (the Hu-IFN-γR1 cDNA) and pγR2 as templates in the same reaction mixture. The second round of the PCR was performed with the set of primers 5'-GACCCTCTTTCCCAGCTGC-3' (SEQ ID NO:10) and 5'-GCCACACATCCTCTTTACGC-3' (SEQ ID NO:11) with 1 μl of PCR reaction mixture from the first round of PCR as template. The final γR2/γR1 PCR product was digested with BstEII restriction endonuclease and cloned into BstEII and blunt-ended XbaI sites of the pγR2 plasmid. The expression vector was designated pγR2/γR 1.

To introduce an NheI site in the beginning of the transmembrane domain of the Hu-IFN-γR2 cDNA clone, the PCR reaction was performed with two primers 5'-GCCTTTTTTAGTTATTATGTC-3' (SEQ ID NO:12) and 5'-ATCGCTAGCCATTGCTGAAGCTCAGTGGAGG-3' (SEQ ID NO:13) and plasmid pγR2 as a template according to a standard protocol [Sambrook et al., *Molecular Cloning: A Laboratory Manual* (1989)]. The PCR product was digested with BstXI restriction endonuclease and ligated into BstXI and EcoRV sites of the pγR2. The plasmid was designated pγR2NheI.

To construct chimeras Hu-IFN-γR2/Hu-IFN-αR1, Hu-IFN-γR2/Hu-IFN-αR2, and Hu-IFN-γR2/CRFB4, the PCR reactions were performed with SP6 primer and 5'-GTGGCTAGCTATAGTTGGAATTTGTATTGC-3' (SEQ ID NO:14) or 5'-GTGGCTAGCATAATTACTGTGTTTTTGAT-3' (SEQ ID NO:15) or 5'-GTGGCTAGCCGTCATCCTCATGGCCTCG-3' (SEQ ID NO:16) primers with plasmids pαR1, pαR2 or pCRF, respectively, as templates. The Hu-IFN-αR1 and Hu-IFN-αR2 PCR products were digested with NheI and ApaI restriction endonucleases and ligated into NheI and ApaI sites of the pγR2NheI. The CRFB4 PCR product was digested with NheI and XbaI restriction endonucleases and ligated into NheI and XbaI sites of the plasmid pγR2NheI. The plasmids were designated pγR2/αR1, pγR2/αR2 and pγR2/CRF, respectively.

To create chimera Hu-IFN-γR2/IL-2Rγ$_c$, the γ$_c$ chain of IL-2R [Takeshita et al., Science, 257:379–382 (1992)] was obtained by RT-PCR as follows. The first strand cDNA synthesis in RT-PCR was performed with poly(dT)$_{18}$ primer with M-MulV reverse transcriptase with total RNA isolated from peripheral blood leukocytes as template. Two PCR rounds were performed. The primers 5'-CGGTTCAGGAACAATCGG-3' (SEQ ID NO:17) and 5'-CAAGCGCCATGTTGAAGCC-3' (SEQ ID NO:18) were used for the first round. For the second round the PCR product from the first round was diluted 100-fold and used as a template for the second round with primers 5'-GTTAGTACCACTTAGGGC-3' (SEQ ID NO:19) and 5'-GTGGCTAGCATGGGAAGCCGTGGTTATC-3' (SEQ ID NO:20). The IL-2Rγ$_c$PCR product was digested with NheI restriction endonuclease and ligated into the NheI and blunt ended XbaI sites of plasmid pγR2NheI. The resultant expression vector was designated pγR2/γ$_c$. The nucleotide sequences of the modified regions of all the constructs were verified in their entirety.

Cells, Media and Transfection. The 16-9 hamster x human somatic cell hybrid line is the Chinese hamster ovary cell (CHO-K1) hybrid containing a translocation of the long arm of human Chromosome 6 encoding the HUIFNGR1 (Hu-IFN-γR1) gene and a transfected human HLA-B7 gene [Soh et al., Proc. Natl. Acad. Sci. USA, 90:8737–8741 (1993)]. The 16-9 cells were maintained in F12 (Ham) medium (Sigma) containing 5% heat-inactivated fetal bovine serum (Sigma) (complete F12 medium). HEp-2 cells, a human epidermoid larynx carcinoma cell line, and COS-1 cells, a SV40 transformed fibroblast-like simian cell line, were maintained in DMEM medium (GIBCO) with 10% heat-inactivated fetal bovine serum.

The 16-9 cells were stably transfected with the expression vectors (1–3 μg of super-coiled plasmid DNA per $10^5$–$10^6$ cells) with LipofectAMINE™ Reagent (Life Technologies) according to the manufacturer's instructions for stable transfection of adherent cells. For cotransfection we used 1–3 μg of plasmid DNA with the neo$^R$ gene and a 10-fold excess of plasmid DNA without neo$^R$ gene per $10^5$–$10^6$ cells. All cell lines transfected with plasmids carrying the neo$^R$ gene were selected and maintained in complete F12 medium containing 450 μg/ml of antibiotic G418. COS-1 cells were transiently transfected with the expression vectors by the DEAE-dextran procedure with DMSO shock [Seed et al., Proc. Natl. Acad. Sci. USA, 84:3365–3369 (1987); Sussman et al., Mol. Cell. Biol., 4:1641–1643 (1984)].

Cytofluorographic Analysis. Cytofluorographic analysis of cells for expression of the HLA-B7 surface antigen was performed as described previously [Jung et al., Somatic Cell and Molecular Genetics, 14:583–592 (1988); Cook et al., Proc. Natl. Acad. Sci. USA, 89:11317–11321 (1992); Hibino et al., J. Biol. Chem., 267:3741–3749 (1992)]. Hu-IFN-αA/D, a chimeric human interferon active on hamster cells [Rehberg et al., J. Biol. Chem., 257:11497–11502 (1982)], was used as a control to demonstrate the integrity of the HLA-B7 gene in various cell lines.

Cross-linking of IFN-γ to Receptors. Recombinant Hu-IFN-γ with a specific activity of 2×$10^7$ units/mg was phosphorylated as reported [Rashidbaigi et al., Proc. Natl. Acad. Sci. USA, 83:384–388 (1986); Mariano et al., in Cytokines: A Practical Approach, 95–108, (1991)]. The [$^{32}$P]Hu-IFN-γ was bound to cells and then crosslinked as described previously [Kotenko et al., supra].

Antibodies. Rabbit anti-Jak1, anti-Jak2 and anti-Jak3 antibodies were developed against synthetic peptides KTLI-EKERFYESRCRPVTPSC (SEQ ID NO:21), DSQRKLQ-FYEDKHQLPAPKC SEQ ID NO:22) and AKLLPLD-KDYYVVREPG (SEQ ID NO:23) corresponding to the end of the kinase-like domains of murine Jak1 and Jak2, and a to sequence within the kinase domain of murine Jak3, respectively. Rabbit anti-Tyk2 antibody was from Santa Cruz Biotechnology (catalog #SC-169). Rabbit anti-Stat1α antibody was raised against the C-terminus of Stat1α. Monoclonal anti-phosphotyrosine antibody was from Sigma (catalog #P3300). Rabbit anti-Hu-IFN-γR2 antibody was prepared with the extracellular domain of Hu-IFN-γR2 as antigen.

Immunoprecipitations, Blottings and Kinase Assay. Cells were starved overnight in serum free media and subsequently stimulated with Hu-IFN-γ (1000 units/ml) for 10 minutes at 37° C. Preparation of cell lysates, immunoprecipitations, blottings and in vitro kinase activation assay were performed as described [Kotenko et al., supra].

Electrophoretic Mobility Shift Assays (EMSA). EMSAs were performed with a 22 base pair sequence containing a Stat1α binding site corresponding to the GAS element in the promoter region of the human IRF-1 gene (5'-GATCGATTTCCCCGAAATCATG-3') (SEQ ID NO:24) as described [Kotenko et al., supra].

Results

Figure 2:
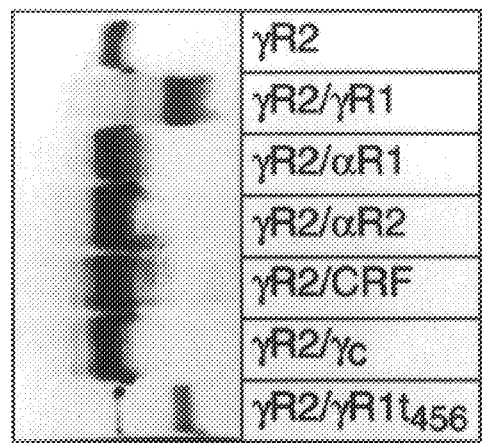
FIG. 2. Expression of Chimeric Receptors in COS-1 Cells. COS-1 cells were transfected with the expression vectors encoding different chimeric receptors: γR2, γR2/αR1, γR2/αR2, γR2/CRF, γR2/Rγ$_c$, γR2/γR1 and γR2/γR1t$_{456}$. The intracellular domain of the chimera γR2/γR1t$_{456}$ represents the intracellular domain of Hu-IFN-γR1 terminated by premature stop codon after amino acid 456 [Kotenko et al., J. Biol. Chem. 270:20915–21 (1995)]. Cells were harvested after three days and lysed as described under "Experimental Procedures" in Example 1. Lysates were resolved on SDS-PAGE, transferred to PVDF membranes and Western blots probed with anti-Hu-IFN-γR2 antibodies.

Construction of Chimeric Receptors, Expression in COS Cells and Crosslinking. To investigate the specific requirements for the intracellular domain of Hu-IFN-γR2 we created chimeric receptors with the extracellular domain of Hu-IFN-γR2 attached to the transmembrane and intracellular domains of different human receptors as shown in FIG. 1. The following receptors were used: two chains of the Hu-IFN-γ receptor complex, Hu-IFN-γR1(γR1) [Aquet et al., Cell 55:273–280 (1988)] or human IFN-γR1t$_{456}$ (γR1t$_{456}$) the truncated γR1 with the intracellular domain terminated by premature stop codon after amino acid 456 [Cook et al., supra ], and Hu-IFN-γR2 (γR2) [Soh et al., Cell, 76:793–802 (1994)]; two chains of human IFN-α receptor complex, Hu-IFN-αR1 (αR1) [Uzéet al., Cell, 60:225–234 (1990)] and Hu-IFN-αR2 (αR2) [Novick et al., supra]; Hu-CRFB4, a class II cytokine receptor with unknown function [Lutfalla et al., supra]; and Hu-IL-2 receptor γ$_c$ chain [Takeshita et al., supra ]. To confirm that all chimeric receptors can be expressed properly, the ability of expression vectors encoding chimeric receptors to express the proteins was determined. All plasmids were transiently transfected into COS-1 cells and the expression of the receptors were evaluated. The cellular lysates from COS-1 cells transiently transfected with the expression vectors were resolved on SDS-PAGE, transferred to membrane and probed with antibodies to the Hu-IFN-γR2 extracellular domain as all these chimeric receptors contain the Hu-IFN-γR2 extracellular domain. In all cases specific bands were detected (FIG. 2). Thus, all vectors encoding the chimeric receptors express these proteins.

Figure 3A:
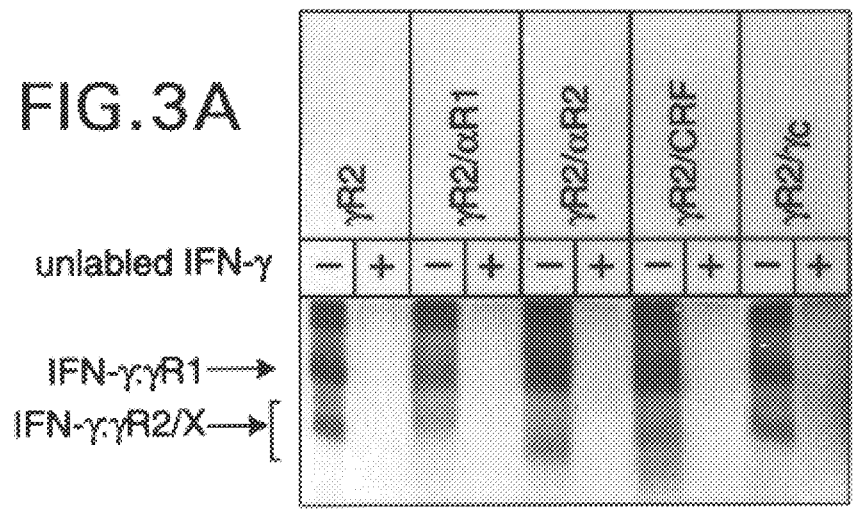
FIG. 3. Covalent Cross-linking of [$^{32}$P]IFN-γ to the Receptors. Cells were harvested and incubated with [$^{32}$P]Hu-IFN-γ with or without addition of a 200-fold excess of unlabeled Hu-IFN-γ and cross-linked as described under "Experimental Procedures" in Example 1. The extracted ligand:receptor complexes were analyzed on a 7.5% SDS-polyacrylamide gel. The cell lines indicated on the figure represent the 16-9 hamster cells (expressing the exogenous Hu-IFN-γR1 chain) transfected with plasmids encoding different second receptor chains: γR2; γR2/γR1, γR2/γR1t$_{456}$, γR2/αR1, γR2/αR2, γR2/CRF and γR2/γ$_c$. The arrows designate the complexes of Hu-IFN-γ with different receptors: γR1, γR2, γR2/αR1, γR2/αR2, γR2/CRF, γR2/γ$_c$, γR2/γR1 and γR2/γR1t$_{456}$.
Figure 3B:
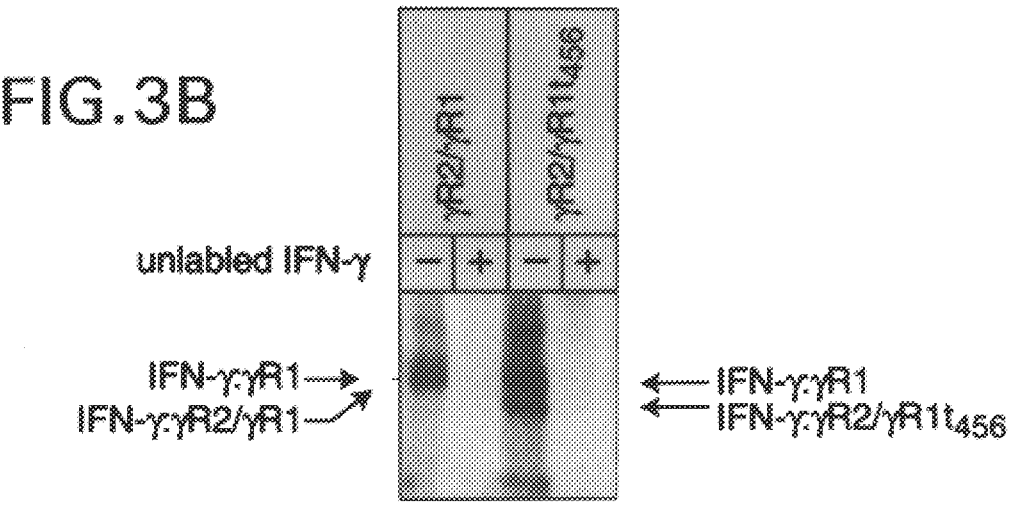

It was previously shown that the Hu-IFN-γR2 chain is a part of the human IFN-γ receptor ligand binding complex, although by itself does not bind Hu-IFN-γ; nevertheless, the Hu-IFN-γR2 chain can be detected by crosslinking to Hu-IFN-γ [Kotenko et al., supra]. Therefore, crosslinking was used to ascertain that the chimeric receptors were expressed on the cell surface and were able to participate in the human IFN-γ receptor ligand binding complex (FIG. 3). All chimeric receptors were stably expressed in 16-9 cells, hamster cells expressing the Hu-IFN-γR1 chain [Soh et al., *Proc. Natl. Acad. Sci. USA,* 90:8737–8741 (1993)], and antibiotic G418-resistant cell populations were used in crosslinking experiment. The cell lines were designated according to the extracellular/intracellular domains (e.g., γR2/γR1) of the chimeric receptors expressed (FIG. 1). The crosslinking of labeled IFN-γ to the parental 16-9 cells results in formation of a single crosslinked band on the SDS-PAGE migrating in the region of 120 kD and corresponding to the Hu-IFN-γ:Hu-IFN-γR1 (IFN-γ:γR1) complex [Kotenko et al., supra]. It was shown that the additional band observed in the γR2 cells migrating in the region of 60 kD corresponded to the Hu-IFN-γ:Hu-IFN-γR2 (IFN-γ:γR2) complex [Kotenko et al., supra]. In addition to the IFN-γ:γR1 crosslinked complex observed in all cell lines (FIG. 3), the mobility of the second band corresponded to the IFN-γ:γR2/X complex (where X represents the transmembrane and intracellular domains of the chimeric receptor expressed) and was different for each chimeric receptor (FIG. 3). The IFN-γ:γR2/X complex was observed for all chimeric receptors, indicating that they all were expressed on the cell surface and formed ternary ligand-receptor complexes (γR1:IFN-γ:γR2/X) in all cell lines. Because the Hu-IFN-γ:γR2/γR1 complex has almost the same mobility as the Hu-IFN-γ:γR1 complex formed from the endogenous Hu-IFN-γR1, in γR2/γR1 cells a single crosslinked band in the region of 120 kD (FIG. 3, right panels) was observed. In addition, in the 16-9 cells transfected with the γR2//γR1t$_{456}$ (γR2/γR1chimera, containing a truncated γR1 intracellular domain, γR1t$_{456}$), the appearance of a faster migrating band representing a cross-linked complex migrating faster than the Hu-IFN-γ:γR2/γR1 complex (FIG. 3, right panels) was observed.

Class I MHC Antigen Induction. Class I MHC antigen (HLA-B7 surface antigen) induction was measured to evaluate the ability of the chimeric receptors to support signal transduction upon Hu-IFN-γ treatment in the 16-9 cells transfected with different chimeric receptors. The 16-9 cells, expressing only the Hu-IFN-γR1 chain of the Hu-IFN-γ receptor complex, exhibited little or no response to Hu-IFN-γ (FIG. 4A). The 16-9 cells were transfected with an expression vector encoding the intact Hu-IFN-γR2 (γR2) or the chimeric receptors Hu-IFN-γR2/Hu-IFN-γR1 (γR2/γR1), Hu-IFN-γR2/Hu-IFN-γR1t$_{456}$ (γR2/γR1t), Hu-IFN-γR2/Hu-IFN-αR1 (γR2/αR1), Hu-IFN-γR2/CRFB4 (γR2/CRF), Hu-IFN-γR2/IL-2Rγ$_c$ (γR2/γ$_c$) to obtain stable transformants. In addition, 16-9 cells were cotransfected with an expression vector encoding Hu-IFN-γR2/IL-2Rγ$_c$ and an expression vector encoding murine Jak3 (γR2/γ$_c$+Jak3). These stable transformants exhibited a significant response to Hu-IFN-γ (FIGS. 4B, C, D, E, G, H, I). For all responsive cell lines the histograms represent the data for clonal cell populations. The Hu-IFN-γ did not induce MHC class I antigens in 16-9 cells stably transfected with the expression vector encoding the Hu-IFN-γR2/Hu-IFN-αR2 (γR2/αR2) chimera (FIG. 4F). As a control, it was shown that all cells responded to Hu-IFN-αA/D demonstrating that the MHC class I antigen could be induced in all cell lines (data not shown).

The Recruitment of Different Jaks into the IFN-γ Receptor Complex. It was reported that different receptors are associated with different Jak family members. Particularly, Hu-IFN-αR1associates with Tyk2 [Barbieri et al., supra; Colamonici et al., *Mol. Cell. Biol.,* 14:8133–8142 (1994)], Hu-IFN-γR2 associates with Jak2 [Kotenko et al., supra] and IL-2Rγ$_c$ associates with Jak3 [Russell et al., supra; Miyazaki et al., supra; Tanaka et al., supra]. Jak1 was shown to associate Hu-IFN-γR1 [Igarashi et al., *J. Biol. Chem.,* 269:14333–14336 (1994); Sakatsume et al., *J. Biol. Chem.,* 270:17528–17534 (1995)] and reported to associate with Hu-IFN-αR2 [Novick et al., supra]. In addition, Hu-IFN-γR1 probably weakly associates with Jak2 after oligomerization upon ligand binding [Kotenko et al., supra]. The ability of the intracellular domains of different receptors fused to the Hu-IFN-γR2 extracellular domain to recruit different members of the Jak family into the Hu-IFN-γ receptor complex and to determine if the recruited Jaks can be activated upon Hu-IFN-γ treatment was tested. First, the phosphorylation of Jak2 upon Hu-IFN-γ treatment in the cell lines expressing various chimeric receptors (FIG. 5A) was determined. The phosphorylation of Jak2 in response to Hu-IFN-γ in cells was examined by immunoprecipitation with specific anti-Jak2 antibodies, followed by a western blot visualized with anti-phosphotyrosine antibodies. The phosphorylation of Jak2 only in γR2 cells (FIG. 5A) was detected.

Inability to detect Jak2 activation in 16-9 cell lines responsive to Hu-IFN-γ containing the chimeric receptors γR2/αR1 and γR2/CRF suggested involvement of other Jaks in these cells. Since the Hu-IFN-αR1 associates with Tyk2 [Barbieri et al., supra; Colamonici et al., supra], Tyk2 activation in cells expressing the chimeric γR2/αR1 chain was evaluated. With anti-Tyk2 antibodies which were developed against human Tyk2, weak phosphorylation of a protein of ~130 kD was detected which was precipitated with anti-Tyk2 antibodies in the cells expressing γR2/αR1 and γR2/CRF (FIG. 5B). When the same blot was reprobed with anti-Tyk2 antibodies, these phosphorylated proteins corresponded to a band recognizable by anti-Tyk2 antibodies and likely represented hamster Tyk2 (FIG. 5B, lower panels), but these proteins migrated slightly slower than human Tyk2 from lysates of COS-1 cells transiently transfected with a plasmid encoding human Tyk2 (data not shown). We observed the phosphorylated proteins of the same size in γR2/αR1 and γR2/CRF cells when immunoprecipitation was performed with anti-phosphotyrosine antibodies and the blot was probed with anti-Tyk2 antibodies (FIG. 5C). The same differences in mobility of hamster Tyk2 from human Tyk2 from control lysates of COS-1 cells transiently transfected with a plasmid encoding human Tyk2 were observed (FIG. 5C).

Figure 5E:
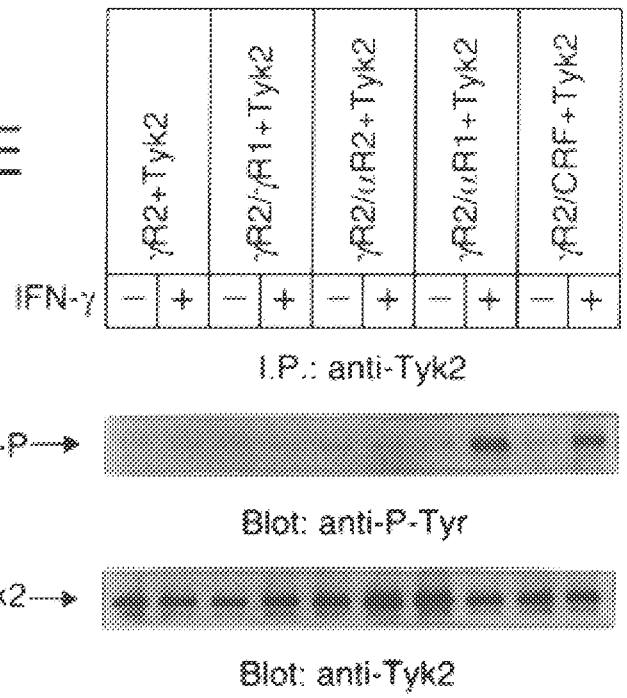
FIG. 5. Tyrosine Phosphorylation of Jaks upon IFN-γ Treatment. Untreated and Hu-IFN-γ treated cells were lysed and immunoprecipitated with anti-Jak2 (A), anti-Tyk2 (B, D and E), anti-Jak3 (F) and anti-phosphotyrosine antibodies (D) as described under "Experimental Procedures" in Example 1. The cell lines are as indicated on the figure and defined in the legends to FIG. 3 and 4. In addition, the γR2/X+Tyk2 cell lines represents 16-9 cells cotransfected with the designated expression vectors encoding γR2/X receptors and human Tyk2; and the γR2/X+Jak3 cell line, 16-9 cells cotransfected with designated expression vectors encoding γR2/X receptors and Jak3. Immunoprecipitates were resolved on SDS-PAGE, transferred to PVDF membranes and probed with various antibodies:anti-phosphotyrosine antibodies, first panels in A, B, D, E and F; with anti-Jak2 antibodies, second panel in A; with anti-Tyk2 antibodies, C, D and second panels in B and E; and with anti-Jak3 antibodies, second panel in F.
Figure 5F:
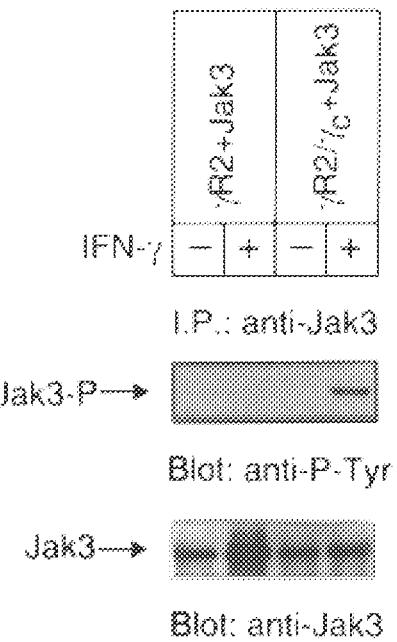

To confirm that the phosphorylated protein in γR2/αR1 and γR2/CRF cells was activated Tyk2, we stably cotransfected a plasmid encoding γR2/αR1 1 or γR2/CRF with a plasmid encoding human Tyk2 into the 16-9 cells. The new cell lines were designated γR2/αR1+Tyk2 and γR2/CRF+Tyk2, respectively. As controls we also cotransfected a plasmid encoding either γR2, γR2/γR1 or γR2/αR2 with a plasmid encoding human Tyk2 into the 16-9 cells. The resultant cell lines were designated γR2+Tyk2, γR2/γR1+Tyk2 and γR2/αR2 +Tyk2, respectively. First, we performed immunoprecipitation with anti-Tyk2 antibodies from cellular lysates prepared from γR2/αR1+Tyk2 and γR2/αR1 cells to evaluate the expression of exogenous human Tyk2 and endogenous hamster Tyk2. After blotting with anti-Tyk2 antibodies it was observed that human Tyk2 was expressed at a much higher level or was able to be precipitated with the antibodies to a greater extent than hamster Tyk2. We also observed the same differences in mobility of human Tyk2 expressed in the 16-9 cells and hamster Tyk2 as we observed above with Tyk2 expressed in COS-1 cells (FIG. 5D). With these cell lines, we observed weak phosphorylation of Tyk2 in untreated γR2/αR1+Tyk2 and γR2/CRF+Tyk2 cells as well as in untreated and treated γR2+Tyk2, γR2/γR1+Tyk2 and γR2/αR2+Tyk2 cells. This is in agreement with the observation that overexpression of members of Jak family causes a low spontaneous level of phosphorylation of kinases in the absence of ligand [Watling et al., supra; Müller et al., Nature, 366:129–135 (1993); Silvennoinen et al., supra]. However, only in γR2/60 R1+Tyk2 and γR2/CRF+Tyk2 cells did we observe an enhancement of Tyk2 phosphorylation after Hu-IFN-γ treatment (FIG. 5E). Thus, we showed that the intracellular domains of Hu-IFN-αR1 and Hu-CRFB4 linked to the extracellular domain of γR2 causes activation of Tyk2 instead of Jak2 which is regularly observed during IFN-γ signalling.

The chimeric receptor γR2/γ$_c$ was able to render 16-9 cells responsive to human IFN-γ to a small extent as measured by class I MHC antigen induction (FIG. 4H). It was shown that the IL-2Rγ$_c$ chain associates with Jak3 [Russell et al., supra; Miyazaki et al., supra; Tanaka et al., supra]. Thus, we examined whether Jak3 participates in the IFN-γ receptor complex in γR2/γ$_c$ cells. We hypothesized that failure of Hu-IFN-γ to induce strong MHC class I antigen induction is due to low level of endogenous Jak3 expression in the 16-9 hamster ovary cells since Jak3 is normally only expressed in hemopoietic cells. To test the hypothesis that the low level of Jak3 limited the IFN-γ signalling in γR2/γ$_c$ cells, we stably cotransfected a plasmid encoding γR2/γ$_c$ with a plasmid encoding either Jak1, Jak2, Jak3, or Tyk2 into the 16-9 cells. Cell lines were designated γR2/γ$_c$+Jak1, γR2/γ$_c$+Jak2, γR2/γ$_c$+Jak3 and γR2/γ$_c$+Tyk2, respectively. Upon Hu-IFN-γ treatment, only γR2/γ$_c$+Jak3 cells showed strong enhancement in MHC class I antigen induction upon Hu-IFN-γ treatment (FIG. 4I). All other cell lines showed the same level of responsiveness as γR2/γ$_c$ cells (FIG. 4H). We confirmed the participation of Jak3 in IFN-γ signalling in the γR2/γ$_c$+Jak$^3$ cells by immunoprecipitation experiments. Only in γR2/γ$_c$+Jak3 cells did we observe enhancement in Jak3 phosphorylation after Hu-IFN-γ treatment. After longer exposure, a low spontaneous level of Jak3 phosphorylation was observed in untreated γR2/γ$_c$+Jak3 cells and in treated and untreated γR2+Jak3 cells used as a control similar to Tyk2 phosphorylation observed in cells overexpressing Tyk2 (see above). Thus, we showed that the γR2/γ$_c$ chimeric receptor recruits Jak3 into the IFN-γ receptor complex due to association of the IL-2Rγ$_c$ intracellular domain with Jak3, and that IFN-γ induces phosphorylation of Jak3 in γR2/γ$_c$+Jak3 cells instead of phosphorylation of Jak2. Therefore, the substitution of the intracellular domain of γ$_c$ for γR2 accordingly substitutes Jak3 for Jak2 in the functional IFN-γ receptor complex.

Jak1 was shown to be activated upon IFN-γ treatment by the in vitro kinase activation assay only in cell lines positive in MHC class I antigen induction.

Figure 4:
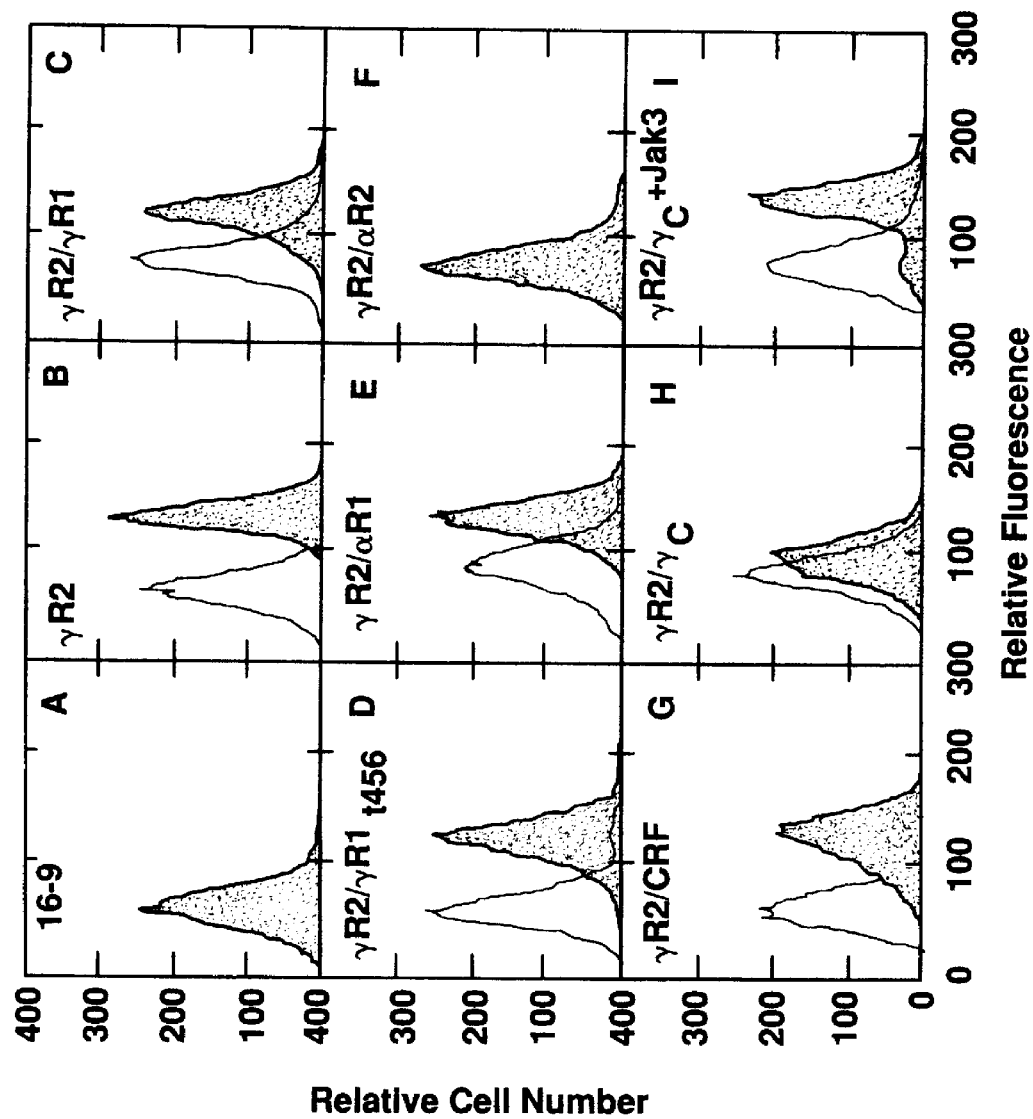
FIG. 4. Induction of HLA-B7 Surface Antigen. Induction of HLA-B7 surface antigen in cells treated with Hu-IFN-γ. The parental 16-9 cells express only exogenous Hu-IFN-γR1(A); the other cells express both γR1 and various receptor chains: γR2 (B); γR2/γR1 (C); γR1/γR1t$_{456}$ (D); γR2/αR1 (E); γR2/αR2 (F); γR2/CRF (G); and γR2/γ$_c$ (H). The γR2/γ$_c$+Tyk2 cell line represents 16-9 cells cotransfected with expression vectors encoding γR2/γ$_c$ and human Tyk2. HLA-B7 antigen was detected by treatment of cells with mouse anti-HLA monoclonal antibody W6/32 followed by treatment with fluorescein isothiocyanate-conjugated goat anti-mouse IgG. The cells were then analyzed by cytofluorography. The unstippled areas represent cells not treated with IFN; stippled areas represent cells treated with 1000 units/ml of Hu-IFN-γ. Relative fluorescence values are shown on a log scale as described [Hibino et al., J. Biol. Chem. 267:3741–3749 (1992)].
Figure 6:
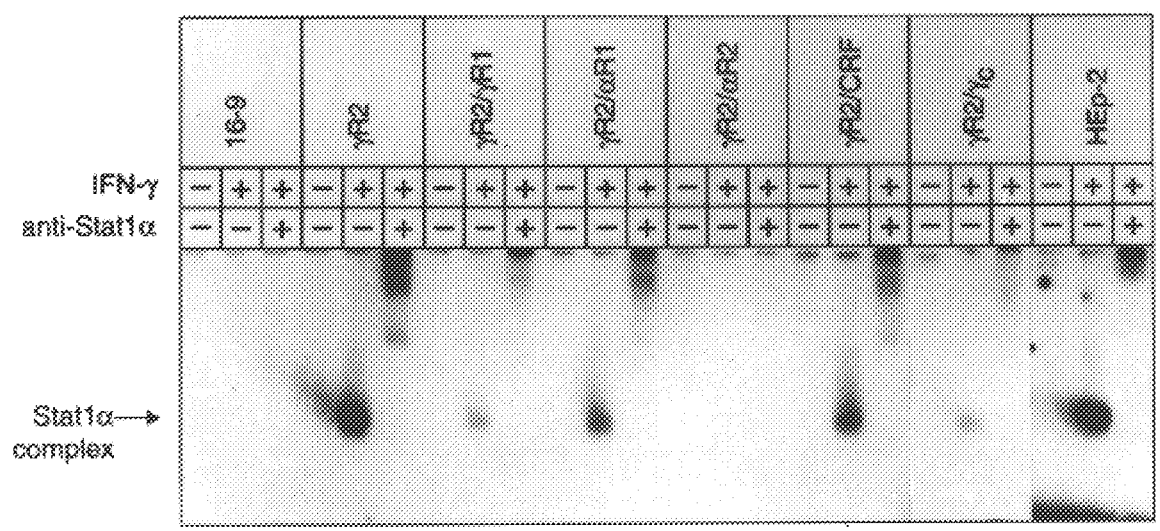
FIG. 6. Electrophoretic Mobility Shift Assay (EMSA). EMSAs were performed as described under "Experimental Procedures" in Example 1 with the 22 base pair labeled sequence containing the Stat1α binding site corresponding to the GAS element in the promoter region of the human IRF-1 gene with nuclear extracts from the cells indicated on the figure and defined in the legend to FIG. 4. In addition, HEp-2 cells, a human epidermoid larynx carcinoma cell line, were used as a positive control. Supershift assays were performed with specific anti-Stat1α antibodies. The position of the Stat1α DNA-binding complexes are indicated by the arrow.

IFN-γ Activates Stat1α through Jak Family Members other than Jak2. It was proposed that Jaks can contribute to the specificity of signal transduction by different IFNs, particularly, Tyk2 (which is active only during Type I IFN signalling) and Jak2 (which is active only during IFN-γ signalling) [Ihle et al., supra]. To evaluate this hypothesis, we performed electrophoretic mobility shift assays with cell lysates prepared from the various transformants before and after treatment with Hu-IFN-γ (FIG. 6). Since Stat1 α homodimer formation occurs during IFN-γ signalling and Stat1α homodimers bind the GAS element with high specificity, we used oligonucleotides corresponding to the GAS element in the promoter region of the human IRF-1 gene as the phosphorylated probe [Yuan et al., Mol. Cell. Biol., 14:1657–1668 (1994)]. The formation of Stat1α DNA binding complexes (FIG. 6) was observed in all cell lines responsive to Hu-IFN-γ as determined by induction of MHC class I antigen (FIG. 4). The Hu-IFN-γ induced activation of Stat1α in γR2/γ$_c$+Jak3 cells was increased to the level comparable to the level of Stat1α activation in all other Hu-IFN-γ responsive cell lines (data not shown).

Because it was shown that other Stats can bind the same GAS element with different affinity [Seidel et al., Proc. Natl. Acad. Sci. USA, 92:3041–3045 (1995)], supershift assays were performed with specific anti-Stat1α antibodies to determine whether the GAS binding complexes observed in the tested cells are formed by Stat1α homodimers. The GAS binding complexes in all tested cells were shifted, indicating that Stat1α was activated in all Hu-IFN-γ responsive cells (FIG. 6).

Discussion

Type I interferons (IFN-α and IFN-β) activate Jak1, Tyk2, Stat1 and Stat2 during signal transduction; Type II interferon (IFN-γ) uses Jak1, Jak2 and Stat1 for signalling [Velazquez et al., supra; Watling et al., supra; Müller et al., Nature, 366:129–135 (1993) and EMBO, 12:4221–4228 (1993); Leung et al., supra]. It was proposed that the utilization of different kinases by a particular receptor complex could contribute to the specificity of signalling by different IFNs [Ihle et al., supra]. To evaluate this hypothesis, a series of experiments with chimeric receptors was undertaken.

The IFN-γ receptor complex whose components and signal partners are now well defined was employed as a model. It has been shown that the active receptor complex consists of two chains of IFN-γR1 (γR1) and likely two chains of IFN-γR2 (γR2) oligomerized upon primary binding of the IFN-γ homodimer to the IFN-γR1 [Greenlund et al., J. Biol. Chem., 268:18103–18110 (1993); Langer et al., Proc. Natl. Acad. Sci. USA, 91:5818–5822 (1994); Marsters et al., Proc. Natl. Acad. Sci. USA, 92:5401–5405 (1995); Walter et al., Nature, 376:230–235 (1995); Kotenko et al., supra]. IFN-γR1 primarily associates with Jak1 [Igarashi et al., supra; Sakatsume et al., supra] and, perhaps, weakly with Jak2 after IFN-γR1 homodimerization [Kotenko et al., supra]. The intracellular domain of IFN-γR2 associates with Jak2 and brings Jak2 into the complex upon ligand binding [Kotenko et al., supra; Sakatsume et al., supra]. The expression of a kinase negative Jak1 mutant in a Jak1 negative (U4A) cell line can sustain an IFN-γ response, indicating that Jak1 predominantly plays a structural role in the normal functional IFN-γ receptor complex rather than catalytic role [Briscoe et al., J. Interferon and Cytokine Res., 15:S56 (1995)]. Thus PTK activity of Jak1 is dispensable for IFN-γ signalling. In contrast, the expression of a kinase negative Jak2 mutant in a Jak 2 negative (γ2A) cell line cannot sustain an IFN-γ response [Briscoe et al., supra], indicating that the PTK activity of Jak2 is absolutely necessary for IFN-γ signalling. Thus, we tested whether substitution of Jak2 by other kinases would change the specificity of signal transduction by IFN-γ. For this purpose the intracellular domains of other receptor chains was substituted for the intracellular domain of Hu-IFN-γR2 to recruit kinases other than Jak2 into the IFN-γ receptor complex. The extracellular domain of Hu-IFN-γR2 was fused to the transmembrane and intracellular domains of either the Hu-IFN-γR1 (γR2/γR1), Hu-IFN-αR1 (γR2/αR1), Hu-IFN-αR2 (γR2/αR2), Hu-CRFB4 (γR2/CRF) or Hu-IL-2Rγ$_c$ chain (γR2/γ$_c$) (FIG. 1). The chimeric chains were expressed in 16-9 cells, Chinese hamster ovary cells expressing Hu-IFN-γR1. By crosslinking [Kotenko et al., supra] it was shown that all chimeric receptors were expressed on the cell surface and were able to participate in formation of the extracellular IFN-γ receptor complex (FIG. 3). We then determined biological responsiveness of the cells to Hu-IFN-γ as measured by MHC class I antigen induction (FIG. 4). The chimeric receptors γR2/γR1, γR2/αR1, γR2/CRF and γR2/γ$_c$ rendered the 16-9 cells responsive to Hu-IFN-γ (FIG. 4C, E, G, H). In contrast, the chimeric receptor γR2/αR2 did not support signal transduction by Hu-IFN-γ (FIG. 4F). Finally, we investigated the activation of Jaks and Stats to determine whether the specificity of signal transduction is altered in cells expressing these chimeric receptors.

In addition to demonstrating that other Jaks can substitute for Jak2 in IFN-γ signal transduction, we provide here evidence that the intracellular domain of CRFB4, a class II cytokine receptor with unknown function [Lutfalla et al., supra (1993)] associates with Tyk2. Therefore, CRFB4 is likely a component of a ligand-receptor system which activates Tyk2 during signal transduction. Tyk2 was shown to be activated by IFN-α, CNTF-related cytokines, IL-10 and IL-12 [Velazquez et al., supra; Barbieri et al., supra; L ütticken et al., supra; Stahl et al., *Science,* 263:92–95 (1994); Finbloom and Winestock, supra; Bacon et al., supra]. Since the components of a given cytokine-receptor complex belong to the same class of the cytokine receptor superfamily, it is most likely that CRFB4 is involved in IFN-α or IL-10 receptor complexes, as all cloned subunits of these receptors are members of the same class as CRFB4 [Uzéet al., supra; Liu et al., *J. Immunol.,* 152:1821–1829 (1994); Novick et al., supra] unlike the components of the CNTF-related cytokine receptor subunits and the IL-12 receptor. Other evidence supports this hypothesis. The reconstitution of an active IFN-α receptor has not been reported [Cohen et al., *Mol. Cell. Biol.,* 15:4208–4214 (1995). However, the yeast artificial chromosome (YAC) containing CRFB4, Hu-IFN-αR1 and Hu-IFN-αR2 genes [Emanuel, Ph.D. Thesis, Rutgers University, Piscataway, N.J. (1995)] encodes a functional Hu-IFN-α receptor complex [Soh et al., *J. Biol. Chem.,* 269:18102–18110 (1994); Cleary et al., *J. Biol. Chem.,* 269:18747–18749 (1994)]. It is thus enticing to consider that these three genes are all involved in Type I interferon receptor function. In the case of IL-10, only one chain (IL-10R) has been cloned [Liu et al., supra]. The activation of two different members of the Jak family during signal transduction usually requires the involvement of two different receptor components associated with two distinct Jaks. Since IL-10 activates Tyk2 and Jak1, CRFB4 may be involved in the IL-10 receptor complex as well. Thus, the use of chimeric receptors provides a method to study the properties of intracellular domains of receptors from unknown or incompletely characterized ligand-receptor complexes as illustrated with the chimeric receptors containing the intracellular domains of Hu-IFN-αR1, Hu-IFN-αR2 or CRFB4.

Figure 7:
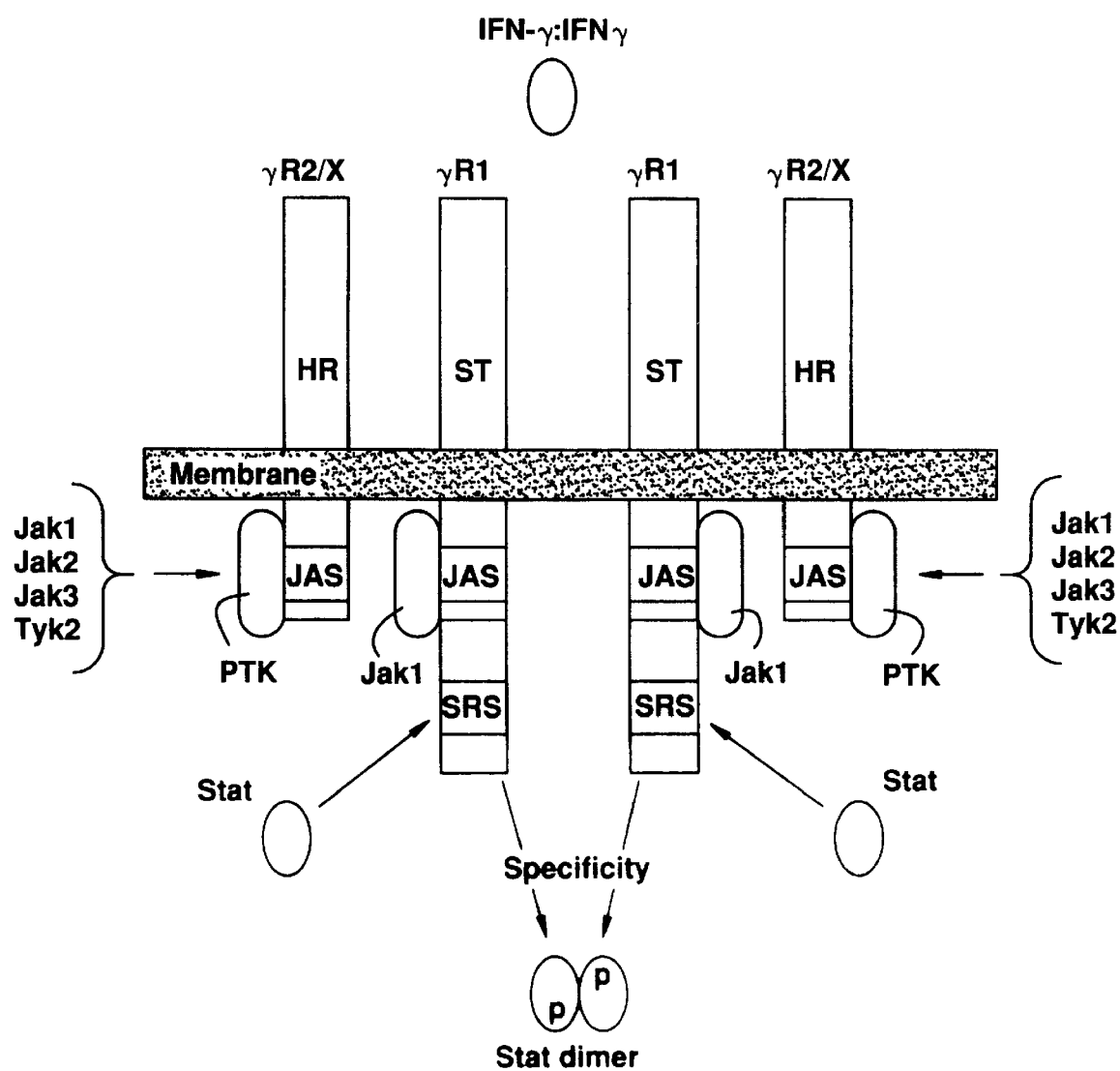
FIG. 7. Model of the Signal Transduction by IFN-γ. After oligomerization of the IFN-γ receptor chains caused by ligand binding, the IFN-γ homodimer binds to two IFN-γR1 chains which in turn brings two associated IFN-γR2 (AF-1) chains and all the associated components (Jaks and Stats) into the complex [Kotenko et al., supra]. The interaction of Jaks with the intracellular chains initiates the cascade of events resulting in activation of specific Stats as described in the text. JAS, represents Jak association site; SRS, Stat recruitment site; ST, signal transducing receptor; HR, helper receptor; PTK, protein tyrosine kinase; γR2/X, chimeric receptor with the extracellular domain of the IFN-γR2 and the intracellular domains of various receptors swapped for the intracellular domain of the Hu-IFN-γR2 chain.

Of most importance, we showed that the Jaks are interchangeable for the Jak-Stat signal transduction pathway. The results allow us to expand our model for IFN-γ signalling [Kotenko et al., supra], which may be general for class II cytokine receptors (FIG. 7). The signal transducing receptor chains can be divided into two classes: (1) the actual Signal Transducers (ST), containing Stat (or other SH2 domain containing protein) Recruitment Sites (SRS) and Jak Association Sites (JAS); and (2) Helper Receptors (HR), containing only JAS, but no SRS. The primary function of the HR is to bring additional PTK activity to the receptor complex upon ligand binding. They do not contain functionally important Tyr residues. Thus far two receptors fit this HR category: the IL-2Rγ$_c$ and IFN-γR2 chains, as it was shown that the substitution of Tyr residues within their intracellular domains does not change the ability of these receptors to support signal transduction [Lai et al., *FASEB J.,* 9:A1021 (5917) (1995); Bach et al., *FASEB J.* 9:A1021 (5919) (1995)]. The CRFB4 chain and probably IFN-αR1 are other candidates for helper receptors. In those cases where homodimerization of a single receptor chain appears sufficient for signal transduction and its intracellular domain contains all the JAS and SRS regions necessary and sufficient for signal transduction (as in the case of EPO-R, GHR or ProR), the activation of a single Jak2 is observed and a separate HR chain is not required [Argetsinger et al., *Cell,* 74:237–244 (1993); Witthuhn et al., *Nature,* 370:153–157 (1993); Campbell et al., *Proc. Natl. Acad. Sci. USA,* 91:5232–5236 (1994); DaSilva et al., *J. Biol. Chem.,* 269:267–270 (1994); David et al., *Proc. Natl. Acad. Sci. USA,* 91:7174–7178 (1994); Dusanter-Fourt et al., *EMBO J.,* 13:2583–2591 (1994); Rui et al., *J. Biol. Chem.,* 269:5364–5368 (1994)]. We hypothesize that the intracellular domains of the HR can be associated with any Jak and do not provide any specificity for signal transduction. Only their extracellular domains are specific for particular ligand receptor complexes. The Jaks show preferential specificity for association with the receptor intracellular domains just like the Stats [Heim et al., supra; Stahl et al., *Science,* 267:1349–1353 (1995)], but the kinase domains per se are promiscuous. Finally, it was hypothesized that the Jaks do not contribute to the specificity of signal transduction in the Jak-Stat pathway, inasmuch as they do not possess a preferential specificity for Stat activation.

EXAMPLE 2

Identification of a Putative Second Chain for a Functional IL-10 Receptor Complex Example 1 shows that the intracellular domain of the CRFB4 chain associates with Tyk2 tyrosine kinase. This observation indicates that the CRFB4 chain is a second chain of human IL-10 receptor (Hu-IL-10R) complex. To evaluate this hypothesis, first, the Hu-IL-10 receptor cDNA (SEQ ID NOS:1 and 2) and CRFB4 cDNA (SEQ ID NOS:3 and 4) were cloned into a mammalian expression vector pEF2 carrying the neo$^R$ marker. In this vector, the transcription of the cDNAs is driven by the powerful promoter of human elongation factor 1α [Mizushima et al., *Nucl. Acids Res.,* 18:5322 (1990)].

Figure 8:
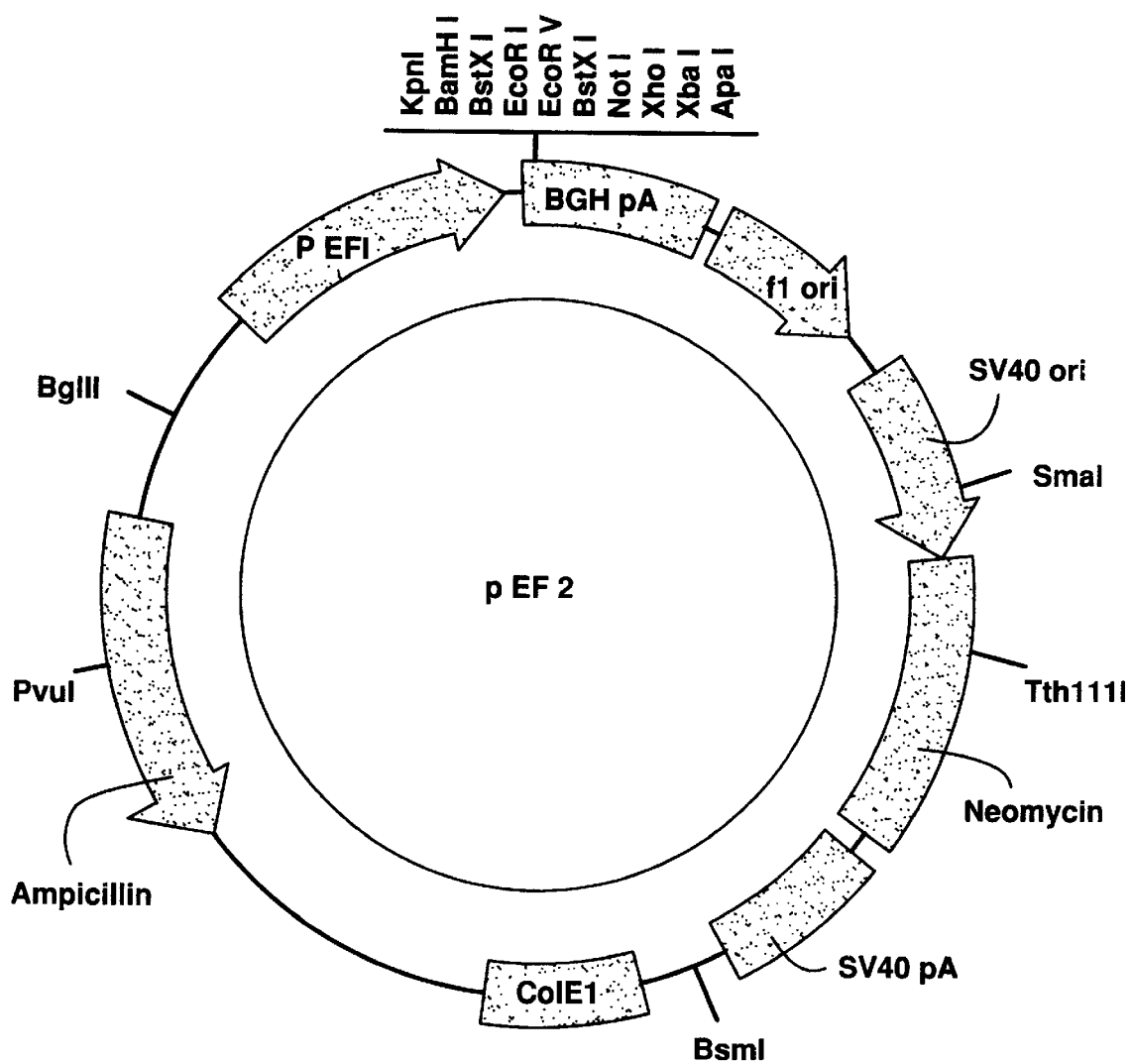
FIG. 8. Map of expression vector pEF2.

The pEF2 vector was created as follows. The CMV promoter was excised from the expression vector pcDNA3 (Invitrogen) with SpeI and EcoRI restriction endonucleases and replaced with the elongation factor 1α (EF1α) promoter excised from the vector pEF-BOS [Mizushima et al., supra] with AvrII and EcoR restriction endonucleases. The intermediate expression vector was designated pEF1. Then all unique cloning sites in the polylinker of the pcDNA3 vector were reconstituted by ligation of the PvuI and blunt ended EcoRI fragment of pcDNA3 into blunt ended HindIII and PvuI sites of the pEF1 vector. The resultant expression vector was designated pEF2 (FIG. 8). The pEF2 vector can produce high level of expression of several receptors: Hu-IFN-γR1, Hu-IFN-γR2, Hu-IFN-αR1 and Hu-IFN-αR2 (data not shown).

The Hu-IL-10R cDNA [Liu et al., *J. Immunol.,* 152:1821–1829 (1994)] was digested with BssHII restriction endonuclease, incubated with the large fragment (Klenow fragment) of DNA polymerase I and four dNTPs and then digested with AvrII restriction endonuclease. The AvrII and blunt ended BssHII fragment of Hu-IL-10R cDNA was ligated into EcoRV and XbaI sites of the pEF2 vector. The expression vector for the Hu-IL-10 R was designated pEF2-IL-10R.

The Hu-CRFB4 cDNA was recloned from plasmid pCRF (Example 1) into plasmid pEF2 with KpnI and XbaI restriction endonucleases. The expression vector for the human CRFB4 transmembrane protein was designated pEF2-CRFB4.

Figure 9:
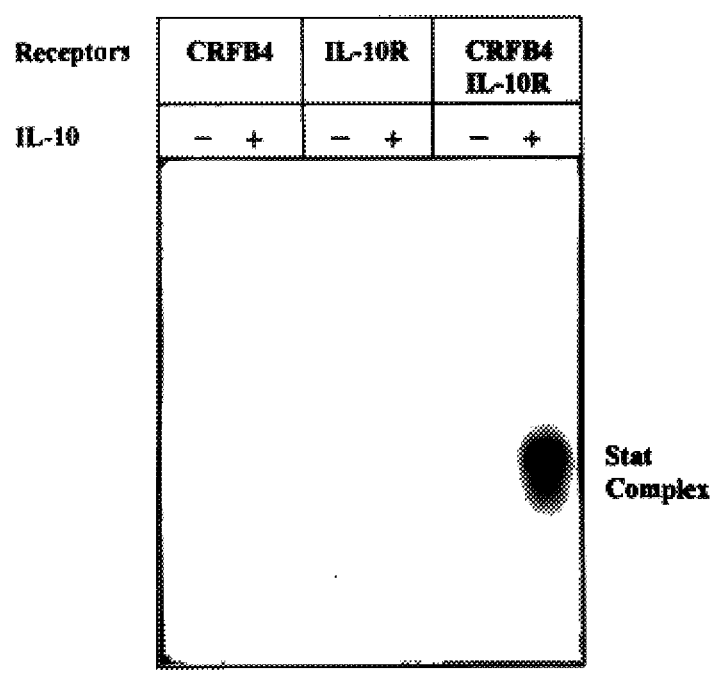
FIG. 9. Electrophoretic mobility shift assay (EMSA). EMSAs were performed as described in Example 1 with total cellular lysates from COS-1 cells treated and untreated with human IL-10. The COS-1 cells were transfected with CRFB4, IL-10R chain, or both CRFB4 and IL-10R chain. Only cells treated with both CRFB4 and IL-10R chain and treated with IL-10 activated Stat1α (labelled "Stat Complex" in the Figure).

The pEF2-CRFB4 and pEF2-IL-10R plasmids were transfected into COS-1 cells separately or together by the DEAE-dextran procedure or by the DMSO shock procedure [Seed et al., *Proc. Natl. Acad. Sci. USA*, 84:3365–3369 (1987); Sussman et al.,*Mol. Cell. Biol.,* 4:1641–1643 (1984)]. Three days after transfection, COS-1 cells were treated with Hu-IL-10 (100 unit/ml). Control cells were left untreated. Total cellular lysates were prepared for the electrophoretic mobility shift assays as described [Kotenko et al., *J. Biol. Chem.,* 270:20915–20921 (1995); Example 1, supra]. It had been shown that IL-10 activates Stat1α and Stat3 during signal transduction [Finbloom et al.,*J. Immunol.,* 155:1079–1090 (1995)]. Thus EMSAs were performed with a 22 base pair sequence containing a Stat1α binding site corresponding to the GAS element in the promoter region of the human IRF-1 gene (5'-GATCGATTTCCCCGAAATCATG-3') (SEQ ID NO:24) as described [Example 1; Kotenko et al., supra]. The formation of Stat DNA binding complexes was detected only in COS-1 cells transfected with both plasmids together and only after IL-10 treatment (FIG. 9). We, therefore, conclude that the presence of the IL-10R and CRFB4 chains is sufficient for signal transduction in response to IL-10; and that the CRFB4 chain is the accessory chain involved in the IL-10 receptor complex.

EXAMPLE 3

MHC Class I Antigen Induction in Hamster Cells in Response to IL-10

The observation that the expression of Hu-IL-10R alone in mouse or COS7 cells [Liu et al., supra] was sufficient to reconstitute some IL-10 signalling suggested that a second chain of the IL-10 receptor complex is expressed widely and is not species-specific between mouse, monkey and human cells. In our experiments with COS1cells transfected with the IL-10R chain, we observed little or no activation of Stat1 and Stat3 (Example 2, FIG. 9). As noted above, when both IL-10R and CRFB4 chains were transfected together into COS1 cells, there was a very nice activation of these Stats.

Figure 10A:
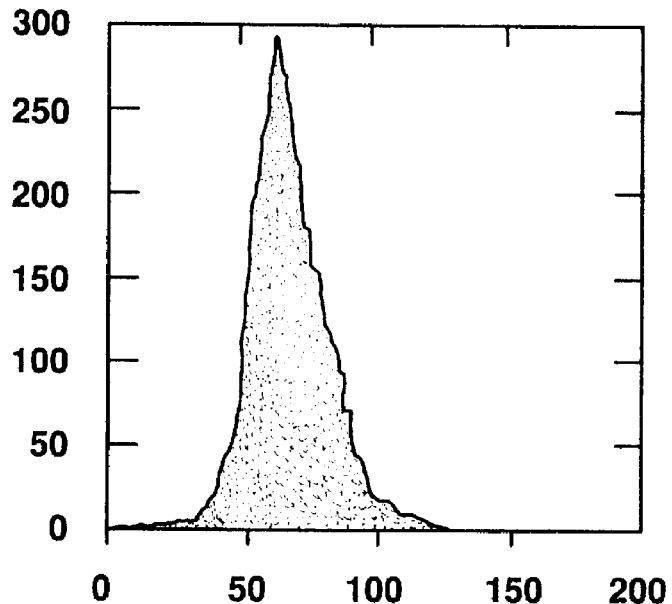
FIG. 10. Induction of HLA-B7 Surface Antigen in Hamster Cells by IL-10. (A) The hamster cells stably transfected with the Hu-IL-10R/γR1 chimeric receptor chain were treated with IL-10 or left untreated. (B) The hamster cells stably transfected with both IL-10R/γR1 chimeric receptor and CRFB4 chains were treated with IL-10 or left untreated. The cells were then analyzed by flow cytometry as described. The unstippled areas represent cells left untreated with IL-10; stippled areas represent cells treated with IL-10. HLA-B7 antigen was detected by treatment of cells with mouse anti-HLA monoclonal antibody W6/32 followed by treatment with fluorescein isothiocyanate-conjugated goat anti-mouse IgG. Relative fluorescence values are shown on a log scale as described [Hibino et al., *J. Biol. Chem.*, 267:3741–3749 (1992)].
Figure 10B:
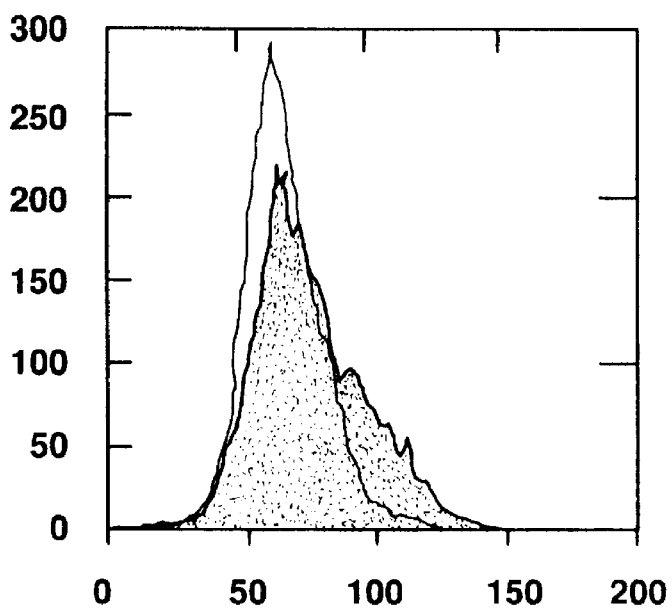

On the other hand, we did not see the activation of Stats in hamster cells stably transfected with IL-10R upon IL-10 treatment as measured by electrophoretic mobility shift assay. Since the activity of IL-10 is restricted to certain cell types [Ho and Moore, *Ther. Immunol.,* 1:173–85 (1994)] and since a ready method to determine the biological activities of IL-10 in hamster cells was not available, a chimeric receptor approach was adopted (see Example 1). The intracellular domain of the IL-10R was substituted with the intracellular domain of the IFN-γR1. To construct chimera IL-10R/γR1, the PCR reaction was performed with 5'-CGGGGTACCCAGGATGCTGCCGTGCC-3' (SEQ ID NO:25) and 5'-ATCGCTAGCCAGTTGGTCACGGTGAAATAC-3' (SEQ ID NO:13) primers. The PCR product was digested with NheI and KpnI restriction endonucleases and ligated into the NheI and KpnI sites of the plasmid pEF2-γR1. The plasmid was designated pEF2-IL-10R/γR1. It was shown that the IFN-γR1 intracellular domain is a signal transducing chain of the IFN-γR1 complex that recruits Stat1α to the complex (Example 1). To enable the IFN-γR1 chain to initiate signalling, the IFN-γR1 chain requires an additional tyrosine kinase activity which is brought into the normal IFN-γ receptor complex on the intracellular domain of the IFN-γR2 (Example 2). Although this function is normally performed by Jak2 kinase associated with the IFN-γR2 intracellular domain, it can also be performed by any tyrosine kinase of the Jak family, including Tyk2, associated with the intracellular domain of the IFN-γR2/X chimeric receptors (Examples 1 and 2). Since Tyk2 is associated with the CRFB4 intracellular domain (Example 2), the IL-10R/γR1 chimeric receptor and CRFB4 chains were postulated to interact upon IL-10 binding so that the intracellular domains of these two chains would mimic the interaction that occurs between the intracellular domains of the normal IFN-γ receptor complex, and would thus initiate signal transduction. Because IFN-γ induces MHC class I antigen expression, we used this cell surface marker to determine if IL-10 would signal through the IL-10R/γR1 chain expressed together with the CRFB4 receptor chain. When the IL-10R/γR1 chimera was expressed alone, it was not able to support signalling upon IL-10 treatment as measured by MHC class I antigen induction (FIG. 10). However, hamster cells stably transfected with both IL-10R/γR1 and CRFB4 chains showed the MHC class I antigen induction in response to IL-10 (FIG. 10). This supports the previous observation that the CRFB4 chain is the second subunit of the IL-10 receptor complex. The CRFB4 chain brings the associated Tyk2 to the IL-10 receptor complex upon IL-10 binding and thus initiates signal transduction by IL-10.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein the disclosures of which are incorporated by reference in their entireties.

What is claimed is:

1. A recombinant DNA molecule comprising a sequence encoding the IL-10 receptor operably associated with an expression control sequence and a sequence encoding CRFB4 operably associated with an expression control sequence.

2. The recombinant DNA molecule of claim 1 wherein the CRFB4 has the amino acid sequence as depicted in SEQ ID NO:4.

3. The recombinant DNA molecule of claim 2, wherein the CRFB4 coding sequence has the nucleotide sequence depicted in SEQ ID NO:3.

4. The recombinant DNA molecule of claim 1, wherein one or both of the expression control sequences comprise the promoter of human elongation factor 1α.

5. A mammalian cell transfected with the DNA molecule of claim 1.

6. A transfected mammalian cell that co-expresses an IL-10 receptor and a recombinant CRFB4 protein, which cell comprises an expression vector comprising a sequence encoding CRFB4 operably associated with an expression control sequence.

7. The mammalian cell of claim 6, wherein the CRFB4 has the amino acid sequence depicted in SEQ ID NO:4.

8. The mammalian cell of claim 7, wherein the CRFB4 coding sequence has the nucleotide sequence depicted in SEQ ID NO:3.

9. The mammalian cell of claim 6, wherein the expression control sequence comprises the promoter of human elongation factor 1α.

10. The mammalian cell of claim 6, which further comprises an expression vector comprising a sequence encoding IL-10 receptor, whereby IL-10 receptor is expressed.

11. A method for identifying a molecule effective as an agonist of IL-10 comprising:

a) contacting the transfected cell of claim 6 with a molecule under consideration as an agonist of IL-10; and b) determining whether the molecule agonizes a functional activity of IL-10;

wherein a molecule that agonizes a functional activity of IL-10 is identified as effective to agonize IL-10.

12. The method according to claim 11 wherein the functional activity of the signal transduction protein of IL-10 comprises activation of Stat1α or Stat3.

13. A method for identifying a molecule effective as an antagonist of IL-10 comprising:

a) contacting the transfected cell of claim 6 with a molecule under consideration as an antagonist of IL-10 and IL-10; and b) determining whether the molecule antagonizes a functional activity of IL-10;

wherein a molecule that antagonizes a functional activity of IL-10 is identified as effective to antagonize IL-10.

14. The method according to claim 13 wherein the functional activity of the signal transduction protein of IL-10 comprises activation of Stat1α or Stat3.

15. A method for identifying a molecule effective as an agonist of IL-10 comprising:

a) contacting the transfected cell of claim 6 with a combinatorial library of molecules;

b) determining whether a molecule selected from said combinatorial library of molecules agonizes a functional activity of IL-10;

wherein the molecule that agonizes a functional activity of IL-10 is identified as effective to agonize IL-10.

16. A method for identifying a molecule effective as an antagonist of IL-10 comprising:

a) contacting the transfected cell of claim 6 with a combinatorial library of molecules;

b) determining whether a molecule selected from the combinatorial library of molecules antagonizes a functional activity of IL-10;

wherein the molecule that antagonizes a functional activity of IL-10 is identified as effective to antagonize IL-10.

* * * * *